US005846768A

United States Patent [19]
Abrams et al.

[11] Patent Number: 5,846,768
[45] Date of Patent: Dec. 8, 1998

[54] INVERTEBRATE APOPTOSIS GENE 'GRIM' AND METHODS OF PRODUCING THE PROTEIN ENCODED THEREBY

[75] Inventors: John M. Abrams; Po Chen; William Nordstrom, all of Dallas, Tex.

[73] Assignee: Board of Regents, The University of Texas System, Austin, Tex.

[21] Appl. No.: 684,101

[22] Filed: Jul. 22, 1996

[51] Int. Cl.$^6$ .......................... C07K 14/435; C12N 1/21; C12N 5/10; C12N 15/12

[52] U.S. Cl. .................. 435/69.1; 435/320.1; 435/172.3; 435/252.3; 435/325; 435/348; 536/23.1; 536/24.3; 536/24.33; 536/24.1; 536/23.5

[58] Field of Search .................................. 536/23.1, 23.5, 536/24.3, 24.33, 24.1; 435/320.1, 69.1, 172.3, 252.3, 325, 348

[56] References Cited

U.S. PATENT DOCUMENTS

| | | | |
|---|---|---|---|
| 5,360,893 | 11/1994 | Owens et al. | 530/350 |
| 5,593,879 | 1/1997 | Steller et al. | 435/240.1 |

OTHER PUBLICATIONS

Abbot, M.K. and J.A. Lengyel, 1991. Embryonic head involution and rotation of the male terminalia require the Drosophila locus head involution defective. *Genetics* 129:783–789.

Abrams J.M., K. White, L. Fessler and H. Steller. 1993. Programmed cell death during Drosophila embryogenesis. *Development* 117:29–43.

Ashburner, "Medfly Transformed—Official!," *Science*, 270:1941–1942, Dec. 1995.

Bump, N.J., M. Hackett, M. Hugunin, S. Seshagiri, K. Brady, P. Chen, C. Ferenz, S. Franklin, T. Ghayur, P. Li, P. Licari, J. Mankovich, L.F. Shi, A.H. Greenberg, L.K. Miller and W.W. Wong. 1995. Inhibition of ICE family proteases by baculovirus antiapoptotic protein p35. *Science* 269: 1885–1888.

Chen, P., et al. 1996 grim, a novel cell death gene in Drosophila. *Genes and Development* 10: 1773–1782.

Clem, R.J., M. Fechheimer and L.K. Miller. 1991. Prevention of apoptosis by a baculovirus gene during infection of insect cells. *Science* 254:1388–1390.

Cleveland, J.L. and J.N. Ihle. 1995. Contenders in FasL/ TNF death signaling. *Cell* 81: 479–82.

Ellis, R.E., J. Yuan and H.R. Horvitz. 1991. Mechanisms and functions of cell death. *Annu. Rev. Cell. Biol.* 7:663–698.

Gavrieli, Y., Y. Sherman and S.A. Ben–Sasson. 1992. Identification of programmed cell death in situ via specific labeling of nuclear DNA fragmentation. *J. Cell. Biol.* 119:493–501.

Golstein, P., D. Marguet and V. Depraetere. 1995. Fas bridging cell death and cytotoxicity: the reaper connection. *Immunol. Rev.* 146:45–56.

Golstein, P., D. Marguet and V. Depraetere. 1995. Homology between Reaper and the cell death domains of Fas and TNFRI, *Cell* 81:185–186.

Gougen, M. and L. Montagnier. 1993. Apoptosis and AIDS. *Science* 260:1269–1270.

Grether, M. J.M. Abrams, J. Agapite, K. White and H. Steller. 1995. The head involution defective gene of *Drosophila melanogaster* and its role in programmed cell death. *Genes and Development* 9: 1694–1708.

Hay, B., T. Wolff and G.M. Rubin. 1994. Expression of the baculovirus p35 prevents cell death in Drosophila. *Development* 120:2121–2129.

Hurle, J.M. 1988. Cell death in developing systems. *Meth. Achiev. exp. Pathol.* 13:55–86.

Kerr, J.F.R., A.H. Wyllie and A.R. Currie. 1972. Apoptosis: a basic biological phenomenon with wide ranging implications in tissue kinetics. *Br. J. Cancer.* 26:239–257.

Liston, P., N. Roy, K. Tamai, C. Lefebvre, S. Baird, G. Chertonhorvat, R. Farahani, M. Mclean, J.E. Ikeda, A. Mackenzie and R.G. Korneluk. 1996. Supression of apoptosis in mammalian cells by naip and a related family of iap genes. *Nature* 379:349–353.

Loukeris, T.G., et al. 1995 Gene transfer into the medfly, *Ceratitis capitata*, with a *Drosophila hydei* transposable element. *Science* 270:2002–2005.

Meyaard, L., S.A. Otto, R.R. Jonker, M.J. Mijinster, R.P.M. Keet and F. Miedema. 1992. Programmed cell death of T cells in HIV–1 infection. *Science* 257:217–219.

Miura, M., H. Zhu, R. Rotello, E.A. Hartwig and J. Yuan. 1993. Induction of apoptosis in fibroblasts by IL–1B–converting enzyme, a mammalian homolog of the C. elegans cell death gene ced–3. *Cell* 75: 653–660.

Oppenheim, R.W. 1991. Cell death during development of the nervous system. *Ann. Rev. Neurosci.* 14:453–501.

Pronk, G.J., K. Ramer, P. Amiri and L.T. Williams. 1996. Requirement of an ice–like protease for induction of apoptosis and ceramide generation by reaper. *Science* 271:808–810.

Rabizadeh, S., D.J. LaCount, P.D. Friesen and D.E. Bredesen. 1993. Expression of the baculovirus p35 gene inhibits mammalian neural cell death. *J. Neurochem.* 61:2318–2321.

Raff, M.C. 1992. Social controls on survival and cell death. *Nature* 356:397–400.

Roy, N., M.S. Mahedevan, M. McLean, G. Shutler, Z. Yaraghi, R. Farahani, S. Baird, A. Besner–Johnson, C. Lefebvre, K. Xiaolin, M. Salih, H. Aubry, K. Tamai, X. Guan, P. Ioannou, T.O. Crawford, P. Jong, L. Surh, J. Ikeda, R.G. Korneluk and A. Mackenzie. 1995. The gene for neuronal apoptosis inhibitory protein is partially deleted in individuals with spinal muscular atrophy. *Cell* 80: 167–178.

(List continued on next page.)

Primary Examiner—Elizabeth C. Kemmerer
Attorney, Agent, or Firm—Arnold, White & Durkee

[57] ABSTRACT

Disclosed is a Drosophila grim gene and encoded GRIM polypeptide, an activator of apoptosis. The disclosed nucleic acid sequences are useful in the production of the protein and as hybridization probes and primers. Expression of the GRIM protein causes programmed cell death. Preferred embodiments include expression of grim under the control of an inducible promoter and the use of such a construct in the control of an insect population.

22 Claims, 2 Drawing Sheets

OTHER PUBLICATIONS

Saunders, J.W., Jr. and J.F. Fallon, 1967, Cell death in morphogenesis, Major problems in Developmental Biology, M. Locke, 289–314, Academic Press, New York.

Sugimoto, A., P.D. Friesen and J.H. Rothman. 1994. Baculoviurs p35 prevents developmentally programmed cell death and rescues a ced–9 mutant in the nematode *Caenorhabditis elegans, EMBO J.* 13:2023–2028.

Touneki, O., J. Belehradek and L.M. Mir. 1995. Relationships between DNA fragmentation, chromation condensation and changes in flow cytometry profiles detected during apoptosis. *Experimental cell research* 217:506–516.

Truman, J. 1984. Cell death in invertebrate nervous systems. *Ann. Rev. Neurosci.* 7: 171–188.

Vito, P., E. Lacana and L. Dadamio. 1996. Interfering with apoptosis—ca2+–binding protein alg–2 and alzheimers disease gene alg–3. *Science* 271:521–525.

White, K., E. Tahaoglu and H. Steller. 1996. Cell killing by the drosophila gene reaper. *Science* 271:805–807.

Williams, G.T. 1991. Programmed cell death: Apoptosis and oncogensis. *Cell* 65:1097–1098.

Wyllie, A.H., J.F.R. Kerr and A.R. Currie. 1980. Cell death: the significance of apoptosis. *Int. Rev. Cytol.* 68:251–306.

Xue, D. and H.R. Horvitz. 1995. Inhibition of the *Caenorhabditis elegans* cell–death protease CED–3 by a CED–3 cleavage site in baculovirus p35 protein. *Nature* 377:248–251.

Zhou, L., H. Hashimi, L.M. Schwartz and J.R. Nambu. 1995. Programmed cell death in the Drosophila central nervous system midline. *Current Biology* 5: 784–90.

Zwiebel, L.J., et al. 1995 The white gene of *Ceratitis capitata*: a phenotypic marker for germline transformation. *Science* 270:2005–2008.

Hengartner. Curr. Opin. Genet. Devp. 6:34–38, 1996.

Steller et al. Neuron 13:1269–1274, Dec. 1994.

Truman et al. J. Neurobiol. 23:1295–1311, 1992.

Steller. Science 267:1445–1449, Mar. 1995.

Zhou et al. PNAS USA 94:5131–5136, May 1997.

Chen et al. Genes Dev. 10:1773–1782, 1996.

Bowie et al. Science 247:1306–1310,1990.

5,846,768

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1677 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( i x ) FEATURE:
        ( A ) NAME/KEY: CDS
        ( B ) LOCATION: 313..727

( x i ) SEQUENCE DESCRIPTION: SEQ ID NO:1:

```
AGTCCACTCT  GAAACCTCGA  CGAGAGAACA  TTGAATAACA  AGCGGAAGCG  AAAAGCGCAG         60

TTGAAAGTTC  GTCAAAAAGC  GACAAGTTTC  CTCGTTCGTT  TTCCCGCCAA  ATGAGTCAGA        120

AAAATTTTCC  AAGTGCTCGA  TACGAAACAT  AAAGACTTAC  AAGACTTAAA  GTGCAAGCAG        180

TGAATGGAAT  ATATTATTCC  TCAGCGATAT  TGAAATCAAA  CATTAAAAAT  ATATGCTACA        240

CTAAAGTTAT  ATATTTTTT  AAAGATTCAT  ACGTTTTGTA  AAATCACATT  TTATATTAAA         300

TTAAATACCG  CC  ATG  GCC  ATC  GCC  TAT  TTC  ATA  CCC  GAC  CAG  GCC  CAA    348
                Met  Ala  Ile  Ala  Tyr  Phe  Ile  Pro  Asp  Gln  Ala  Gln
                 1              5                         10

TTG  TTG  GCC  AGA  AGC  TAT  CAG  CAA  AAC  GGC  CAG  CAG  ACA  GCA  GCG  AGT    396
Leu  Leu  Ala  Arg  Ser  Tyr  Gln  Gln  Asn  Gly  Gln  Gln  Thr  Ala  Ala  Ser
              15                        20                    25

CCA  AGG  ACG  ACT  GCA  ACA  GCT  GCT  GCA  CCA  TCG  CAG  CAG  CAG  CAA  CAA    444
Pro  Arg  Thr  Thr  Ala  Thr  Ala  Ala  Ala  Pro  Ser  Gln  Gln  Gln  Gln  Gln
         30                        35                        40

TCG  CAA  CAA  CAG  CAG  CAG  CAG  CAG  CGA  CAT  CAT  CAT  CAG  CAA  CAG  CGC    492
Ser  Gln  Gln  Gln  Gln  Gln  Gln  Gln  Arg  His  His  His  Gln  Gln  Gln  Arg
 45                      50                        55                      60

CCA  CAA  TTC  CGT  GCC  AAT  ATT  TCC  GTG  CCG  CTG  GGA  AGT  CAA  CAG  GGA    540
Pro  Gln  Phe  Arg  Ala  Asn  Ile  Ser  Val  Pro  Leu  Gly  Ser  Gln  Gln  Gly
              65                        70                        75

TCG  ATG  ACC  ATG  TCG  GAG  TTT  GGA  TGC  TGG  GAT  CTT  TTG  GCC  CAG  ATC    588
Ser  Met  Thr  Met  Ser  Glu  Phe  Gly  Cys  Trp  Asp  Leu  Leu  Ala  Gln  Ile
                   80                        85                        90

TTG  TGC  TAC  GCT  CTG  CGA  ATC  TAC  AGC  TAC  AGT  TCG  AGC  CAG  CGT  CAA    636
Leu  Cys  Tyr  Ala  Leu  Arg  Ile  Tyr  Ser  Tyr  Ser  Ser  Ser  Gln  Arg  Gln
         95                       100                       105

CCG  ACG  GTC  ATT  CAG  ATA  TCC  TTC  GAG  ATC  AGC  AGC  GGC  GGT  CAG  AAC    684
```

```
              Pro  Thr  Val  Ile  Gln  Ile  Ser  Phe  Glu  Ile  Ser  Ser  Gly  Gly  Gln  Asn
                   110                 115                 120

AAC  GAT  GAG  GAC  GAC  GTT  ACC  GAT  GCC  ACC  TCC  AAG  GAG  AAC  T                        727
Asn  Asp  Glu  Asp  Asp  Val  Thr  Asp  Ala  Thr  Ser  Lys  Glu  Asn
125                      130                      135

AAATTTGGTT  TCCATATTTC  ATCCTGGTGG  AGAGAAAATC  TTTGGGATTT  TCTGGGAAAG                           787

GCAGGCTCAA  TCAAAGCGCA  TTGTGATTTC  TTTTTGGGT   ATGGACACAT  GAGGAGGAAC                           847

GAGTTTTGTA  AAACATGGGA  TATTTCCACA  ACAAATAAG   AAAACTATTT  TTAAACTATT                           907

TTTGAGAGAG  AGAAAATTCA  AAATTTGTCA  TCGACTTGCT  TAAAGTGATT  TTGTTTTTTT                           967

GTTACTTTTT  TGGATGTCAA  ATTTTCCGAT  ATAAGTTTTG  AAAAAATGTT  TAATTTTGCA                          1027

AGCAAAGGTT  TCCCGGTTGG  TTCAAATACA  TAAACATACT  TAACAACATT  TAGAGAGCAT                          1087

AAAGAGAAAT  GTGTAAAATT  GTCATAAACC  TTATTAGTGT  CTATATGTAT  GAGCAAAACC                          1147

ACAAGTATCG  TACTCAACTA  ACAAATAATT  GTCAAATTTT  TGCATTTCAA  CTACTTACAA                          1207

ATATAAATCG  TAAACTAATA  TTACAGAACT  ACAATACAGA  ACCAGCAACA  AAACAAAGAT                          1267

GCAACCGCAG  CAACAAGAAT  AACAAAGAC   AACAACTCAA  TTGTACAAAA  TAGATTTTAA                          1327

GCAAACAGCA  AATTTTATAT  GTTTACAACA  AAGAAAGAAA  ATACTAAACG  TCTACAAAAA                          1387

ATAGAATACA  AGAACCGCCG  AACGAAATAC  ATTTTAACAA  AAATTAAACA  AAACAACACA                          1447

TTTAAGCAAT  TTTGATACGA  ATAATCAAGA  ATAACAAAAT  TTGAAATGAA  TCTTATCATT                          1507

ATTATTGATT  TTAGCAAAAT  TCAAAACATA  TTATTTCAAT  TTTGGCATTG  CAAATTAAAC                          1567

AAGAAATATT  GAAATTAATC  ACGTAAAGAT  AGCATTTGTA  AGAAATTAAA  ATTTTTATAA                          1627

GACAAACAAG  CAAAAAATAA  ATACTTTTAT  AAAAAAAAAA  AAAAAAAAAA                                      1677
```

( 2 ) INFORMATION FOR SEQ ID NO:2:

( i ) SEQUENCE CHARACTERISTICS:
    ( A ) LENGTH: 138 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Met  Ala  Ile  Ala  Tyr  Phe  Ile  Pro  Asp  Gln  Ala  Gln  Leu  Leu  Ala  Arg
 1                  5                   10                       15

Ser  Tyr  Gln  Gln  Asn  Gly  Gln  Gln  Thr  Ala  Ala  Ser  Pro  Arg  Thr  Thr
                20                  25                       30

Ala  Thr  Ala  Ala  Ala  Pro  Ser  Gln  Gln  Gln  Gln  Ser  Gln  Gln  Gln
          35                  40                       45

Gln  Gln  Gln  Gln  Arg  His  His  His  Gln  Gln  Gln  Arg  Pro  Gln  Phe  Arg
           50                  55                       60

Ala  Asn  Ile  Ser  Val  Pro  Leu  Gly  Ser  Gln  Gln  Gly  Ser  Met  Thr  Met
 65                      70                  75                       80

Ser  Glu  Phe  Gly  Cys  Trp  Asp  Leu  Leu  Ala  Gln  Ile  Leu  Cys  Tyr  Ala
                     85                  90                       95

Leu  Arg  Ile  Tyr  Ser  Tyr  Ser  Ser  Ser  Gln  Arg  Gln  Pro  Thr  Val  Ile
               100                 105                      110

Gln  Ile  Ser  Phe  Glu  Ile  Ser  Ser  Gly  Gly  Gln  Asn  Asn  Asp  Glu  Asp
          115                     120                      125

Asp  Val  Thr  Asp  Ala  Thr  Ser  Lys  Glu  Asn
         130                     135
```

INVERTEBRATE APOPTOSIS GENE 'GRIM' AND METHODS OF PRODUCING THE PROTEIN ENCODED THEREBY

The government owns rights in the present invention pursuant to grant number AG12466 from the *National Institutes of Health*.

BACKGROUND OF THE INVENTION

1. Field of the Invention

The present invention relates generally to the fields of pest control and molecular biology and, in particular, to genetic control of programmed cell death (PCD), or apoptosis in insect and human cells.

2. Description of Related Art

Programmed cell death (PCD) or apoptosis is an essential regulator of tissue differentiation and cellular maintenance as animals develop and age [Saunders and Fallon, 1967; Truman, 1984; Hurle, 1988; Ellis, et al., 1991; Oppenheim, 1991; Raff, 1992]. Recent studies have implicated the misregulation of apoptosis in the pathophysiology of several human diseases including AIDS [Meyaard, et al., 1992; Gougen and Montagnier, 1993], neurodegenerative disease [Roy, et al., 1995; Liston, et al., 1996; Vito, et al., 1996] and cancer [reviewed in Williams, 1991].

Several lines of evidence suggest that the physiology of apoptosis is quite highly conserved. First, the morphological changes associated with programmed cell deaths are strikingly similar in both vertebrates and invertebrates [Kerr, et al., 1972; Wyllie, et al., 1980; Kerr and Harmon, 1991; Abrams, et al., 1993]. Second, at least two essential cell death genes in *Caenorhabditis elegans*, ced-3 and ced-9, are members of gene families that encode apoptotic functions in vertebrates [reviewed in Steller, 1995; White, 1996]. Third, viral proteins that suppress apoptosis in their hosts (p35 and crmA) can exhibit potent anti-apoptotic activity in a wide range of heterologous species [Rabizadeh, et al., 1993; Hay, et al., 1994; Sugimoto, et al., 1994; Grether, et al., 1995; Pronk, et al., 1996; White, et al., 1996].

In *Drosophila melanogaster*, a genomic interval defined by the H99 deletion mutation is required for embryonic programmed cell death [Abrams, et al., 1993; White, et al., 1994; Abrams, 1996]. This region spans ~300 kilobases of DNA that includes at least two cell death genes, reaper (rpr) [White, et al, 1994] and head involution defective (hid) [Grether, et al., 1995]. The former gene product is thought to share similarities to the "death domain" of the FAS/TNFR1 protein family [Cleveland and Ihle, 1995; Golstein, et al., 1995; Golstein, et al., 1995] whereas the latter shares no extensive sequence similarity to known proteins. Although the distribution of RNA from both genes generally corresponds to embryonic patterns of apoptosis, only rpr appears to be selectively expressed in all cells that will later undergo programmed cell death.

Although no apoptosis occurs in embryos bearing homozygous deletions of the entire H99 interval [Abrams, et al., 1993; White, et al., 1994], null mutations at hid display only mild cell death defects [Grether, et al., 1995] and, to date, no single-gene mutants of the rpr have been identified. Therefore, the precise number of cell death genes uncovered by H99 is not known. In fact, phenotypes associated with two informative deletions in the region, X14 and X25 [White, et al., 1994; Grether, et al., 1995], raised the possibility that perhaps one or more additional cell death genes might reside between hid and rpr. Both strains partially uncover the H99 interval from the distal boundary thereby eliminating hid yet preserving rpr. However, although both deletions exhibit mild and indistinguishable PCD phenotypes as homozygotes [Grether, et al., 1995], X25 uncovers a far more severe phenotype when placed in trans to H99 than does X14. Whereas X14/H99 embryos show subtle cell death defects similar to those observed for hid null alleles, X25/H99 transheterozygotes exhibit a severe reduction in apoptosis frequency that can be easily visualized by staining with acridine orange [Grether, 1994]. Since the relevant breakpoint of X25 is ~60 kb more proximal than that of X14 [Grether, 1994], it is possible that one or more additional cell death functions map to the interval bounded by these breakpoints.

There is still a need therefore, for methods of controlling insect pests without the use of pesticides that remain in the environment and contribute to pesticide resistance, or for methods of controlling apoptosis in cells that have a disrupted apoptotic function by restoration of apoptosis genes. These needs may be met by the discovery of apoptosis controlling genes that are active in insect species and that also may be active in other species, including mammalian and even human cells.

SUMMARY OF THE INVENTION

The present invention seeks to overcome certain drawbacks inherent in the prior art by providing the isolation of a novel Drosophila apoptosis gene, designated as grim. The isolation of this gene allows the production of high levels of the GRIM protein as well as providing methods of inducing apoptosis in various types of cells, including, but not limited to, insect cells, such as insect embryo cells, and human cells. Of particular advantage is the use of the present discovery in conjunction with an inducible promoter so that the apoptosis gene may be inserted into a particular cell line and remain silent until the inducing condition is encountered, at which time the expression of GRIM causes programmed cell death in the recombinant or transgenic cell.

In a certain broad aspect, the present invention is an isolated nucleic acid segment and particularly a nucleic acid segment that encodes a Drosophila GRIM polypeptide. The encoded Grim polypeptide of the present invention may comprise an amino acid sequence of SEQ ID NO:2 or may in certain embodiments have the amino acid sequence of SEQ ID NO:2. The invention may also be described in a certain broad aspect as an isolated nucleic acid segment that comprises a nucleic acid sequence including the coding region of SEQ ID NO:1 or its complement, or even as an isolated nucleic acid segment having a sequence as set forth in SEQ ID NO:1 or its complement. The nucleic acid segments so described may be fused to other functional nucleic acid sequences such as those encoding leader sequences, fusion proteins, epitope tags, ribosomal binding sites, polyadenylation sites, genetic linkers containing restriction enzyme recognition sequences, promoters, selectable markers and a variety of other segments well known in the art.

The complement of a DNA or RNA sequence is well known in the art and is based on the Watson-Crick pairing of nucleic acid polymers. The complement of a nucleic acid segment is generated by converting all "G" residues to "C" residues, all "C" residues to "G" residues, all "A" residues to "T" (in the case of DNA) or "U" (in the case of RNA) and all "T" or "U" residues to "A", and then reversing the 5' to 3' orientation of the generated sequence. As used herein therefore, the term "complement" defines a second strand of nucleic acid which will hybridize to a first strand of nucleic acid to form an antiparallel duplex molecule in which base pairs are matched as G:C, C:G, A:T/U or T/U:A.

The present invention may also be described in certain embodiments as a nucleic acid segment that is hybridizable to the nucleic acid segment of SEQ ID NO:1 or its complement under stringent conditions. Hybridizable is understood to mean the formation of a double stranded molecule or a molecule with partial double stranded structure. Stringent conditions are those that allow hybridization between two nucleic acid sequences with some degree of homology, but precludes hybridization of random sequences. The degree of homology would depend on the length of the sequences to be hybridized. A sequence of from 10 to 14 or even about 20 bases in length would likely tolerate no internal mismatches at high stringency, but longer sequences of up to 50 or 100 bases, for example would tolerate some mismatches as long as stretches of 17–20 or more bases contained within the longer sequences hybridized without mismatches. For example, hybridization at low temperature and/or high ionic strength is termed low stringency and hybridization at high temperature and/or low ionic strength is termed high stringency. Some examples of ranges that may be employed are for low stringency, from 0.15–0.9M NaCl at a temperature of 20°–50° C. might be employed, and for high stringency, from 0.02–0.15M NaCl at a temperature of 50°–70° C. might be employed. It is understood that the temperature and ionic strength of a desired stringency are applicable to particular probe lengths, to the length and base content of the sequences and to the presence of formamide or other solvents in the hybridization mixture and that these ranges are mentioned by way of example only. It is routine practice in the art to hybridize to a target sequence in the presence of a negative control and if possible, a positive control, and the determination of a positive hybridization is often based on a comparison to the two types of controls under identical conditions.

It is understood in the art that a nucleic acid sequence will hybridize with a complementary nucleic acid sequence under high stringency conditions even though some mismatches may be present, particularly in complementary stretches of more than about 15 bases. Such closely matched, but not perfectly complementary sequences are also encompassed by the present invention. For example, differences may occur through genetic code degenerency, or by naturally occurring or man made mutations and such mismatched sequences that hybridize under high stringency conditions would still be encompassed by the present claimed invention.

In certain broad aspects, the nucleic acid segments of the present invention may be under the control of, or operatively linked, to a promoter. The promoter may be the homologous promoter that controls the expression of the segment in its native tissue, or it may be a heterolgous promoter. By heterologous promoter is meant a promoter derived from another source, either another within the same cell or from a different type of cell or even from a different organism. The promoter sequence is then joined to the nucleic acid segment in an upstream position (5') from the start of the gene. It is understood in the art that to bring a coding sequence under the control of a promoter, or to operatively link a gene to a promoter, one positions the 5' end of the transcription initiation site of the transcriptional reading frame of the protein between about 1 and about 50 nucleotides "downstream" (i.e., 3') of the chosen promoter. In addition, where eukaryotic expression is contemplated, one will also typically desire to incorporate into the transcriptional unit which includes the cotransporter protein, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination. Preferred promoters are cytomegalovirus major immediate early gene promoter, simian virus 40 late gene promoter and Baculovirus *Autographa californica* nuclear polyhedrosis virus polyhedrin gene promoter, and even more preferred are inducible promoters such as a heat shock protein promoter, a radiation inducible promoter or a metal inducible promoter. A most preferred promoter in the practice of the present invention is the hsp70 promoter.

The nucleic acid segments of the present invention may also comprise a recombinant vector or even a recombinant expression vector capable of replicating within a cell. In particular, the nucleic acid segment expressing a GRIM polypeptide on introduction into a host cell. A large number of vectors are available commercially and are well known to those in the art. In general, a vector is compatible with a particular cell type such as prokaryotic, eukaryotic, yeast, plant, insect, etc. The matching of compatible vectors and host cells is well known and routinely practiced in the art. The vector may be further defined as comprising the nucleic acid sequence set forth in SEQ ID NO:1 or its complement, or as a recombinant expression vector capable of expressing a GRIM polypeptide on introduction into a host cell.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

As used herein, the term "engineered" or "recombinant" cell is intended to refer to a cell into which a recombinant gene, such as a gene encoding a GRIM polypeptide has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene.

Preferred cell lines to be used in the present invention are eukaryotic cells and more preferred are insect or mammalian cells. Preferred cells for the expression of GRIM polypeptides may include, for example, chinese hamster ovary (CHO), human 293 and Drosophila SL2 cell lines, and more preferred are SF-9 Baculoviral cells. The host cell may be further defined as comprising the nucleic acid segment in accordance with SEQ ID NO:1 or its complement, positioned in a recombinant vector, although it is understood that the nucleic acid segment may also be integrated into the host genome, and in particular, the host cell may be defined as comprising a recombinant expression vector and expressing a GRIM polypeptide.

Of particular interest is the use of insect cells as a host for baculoviral expression vectors. Currently, the preferred baculovirus expression systems utilize the lytic insect virus known as *Autographa californica* multiply enveloped nuclear polyhedrosis virus. For production of recombinants in insect cells using recombinant baculoviral vectors, it is desirable to utilize the polyhedron gene's powerful promoter and control sequences. This can be accomplished by replacing the baculoviral polyhedron gene with the cDNA to be expressed. Baculoviral expression vectors ordinarily include all the original baculoviral genes except the polyhedron gene and may include additional marker genes such as the β-galactosidase gene. Examples of such useful baculoviral preparations include Linearized AcMNPV Baculovirus DNA, Linearized AcRP23.lacZ Baculovirus DNA, and Linearized AcUW1.lacZ Baculovirus DNA. After cloning the cDNA to be expressed in a suitable transfer plasmid, the cDNA can be transferred in place of the baculovirus polyhedron gene by the process of recombination. The transfer plasmids contain baculoviral DNA sequences to promote the recombination with linear baculoviral DNA and may also contain additional marker genes such as the β-galactosidase gene. Suitable transfer plasmids include pBlueBac III, pBlueBacHis, and pAcUW21. The recombination to assemble the recombinant baculovirus which expresses the cDNA of interest and production of the protein product from that cDNA is performed in insect cells or insect hosts. Examples of suitable host cells include *Spondoptera frugiperda Sf9* cells, Sf21 cells, and MG1 cells.

In addition to microorganisms and insects, cultures of cells derived from vertebrate organisms may also be used as hosts. In principle, any such vertebrate or invertebrate cell culture is workable. However, vertebrate cells are a preferred host, and propagation of vertebrate cells in culture (tissue culture) has become a routine procedure in recent years. Examples of such useful host cell lines are VERO and HeLa cells, Chinese hamster ovary (CHO) cell lines, and W138, BHK, COS-7, 293 and MDCK cell lines. Expression vectors for such cells ordinarily include (if necessary) an origin of replication, a promoter located in front of the gene to be expressed, along with any necessary ribosome binding sites, RNA splice sites, polyadenylation sites, and transcriptional terminator sequences.

It is understood that smaller nucleic acid segments which comprise as their nucleic acid sequence the nucleic acid sequence of SEQ ID NO:1 or its complement are also encompassed by the present invention. For example, nucleic acid segments comprising a segment of at least ten, fifteen, seventeen, twenty, thirty, fifty, sixty or even up to about one hundred contiguous nucleotides that correspond to SEQ ID NO:1 or its complement are also a part of the present invention. Such segments are useful as hybridization probes and amplification primers for grim and related genes and other uses well known in the art.

In certain broad aspects, the present invention is a partially purified polypeptide, or protein with an amino acid sequence in accordance with SEQ ID NO:2. The protein may be isolated from natural sources, or it may be expressed from a recombinant vector.

Generally, "partially purified" will refer to a protein composition that has been subjected to fractionation to remove various non-protein components such as cell membrane and other cell components. Various techniques suitable for use in protein purification are well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques.

An important use of the polypeptides of the present invention is the production of antibodies which are immunoreactive with GRIM. These antibodies will have utility as diagnostic agents for the expression of GRIM as well as use as possible inhibitors of apoptosis. Therefore antibodies which are produced with the peptides or polypeptides of the present invention, or those antibodies which are found to be immunoreactive with the peptides or polypeptides of the present invention are also a part of this invention. The antibodies may be polyclonal antibodies or monoclonal antibodies and may be derived from any source such as goat, mouse, bovine, equine, simian or any other source, even including recombinantly produced antibodies. The production of anti-idiotype antibodies is also well known in the art, and any such anti-idiotypic antibodies are also encompassed by the present invention.

In certain broad aspects the present invention may be described as a method for identifying a grim nucleic acid sequence, comprising the steps of obtaining a target nucleic acid segment suspected of containing a grim sequence, hybridizing one or more nucleic acid segments of SEQ ID NO:1 or its complement to said the target segment and detecting the hybridization. In the practice of this method, hybridization is indicative of a grim nucleic acid sequence, especially when hybridization occurs under high stringency conditions as defined above. In certain embodiments of the method, the nucleic acid segments are used as amplification primers and an amplified product is indicative of a grim nucleic acid sequence.

The invention may also be described in certain broad aspects as a method of making a Drosophila GRIM polypeptide. This method comprises the steps of obtaining an expression vector containing a nucleic acid sequence encoding a GRIM polypeptide wherein the nucleic acid sequence is operatively linked to a promoter, transfecting the vector into a host cell and culturing the cell under conditions effective to express the GRIM polypeptide. In preferred embodiments of the method, the promoter is an inducible promoter. In addition, the method of making a GRIM polypeptide may further comprise the step of isolating the GRIM polypeptide.

An aspect of the invention is also a method of decreasing an insect population comprising the steps of obtaining transgenic adults comprising a grim gene operatively linked to an inducible promoter, allowing the adults to interbreed with the population to be controlled and exposing the offspring to conditions effective to induce said promoter. A particularly preferred method includes the use a heat shock promoter, so that the promoter is silent during the cooler months while the recombinant gene is introduced into the population, and is then induced in warm weather, thus killing the embryos.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

As used herein the term nucleic acid segment may refer to a segment of DNA or RNA. A DNA segment is intended to refer to a DNA molecule which has been isolated free of total genomic DNA of a particular species. Therefore, a DNA segment encoding the protein GRIM is intended to refer to a DNA molecule which contains said coding sequence yet is isolated away from total genomic DNA of *Drosophila melanogaster*. An RNA segment is intended to refer to an RNA segment isolated to some degree from the total RNA of a cell. Included within the term "DNA segment", are DNA segments which may be employed in the preparation of vectors, as well as the vectors themselves, including, for example, plasmids, cosmids, phage, viruses, and the like.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1A:
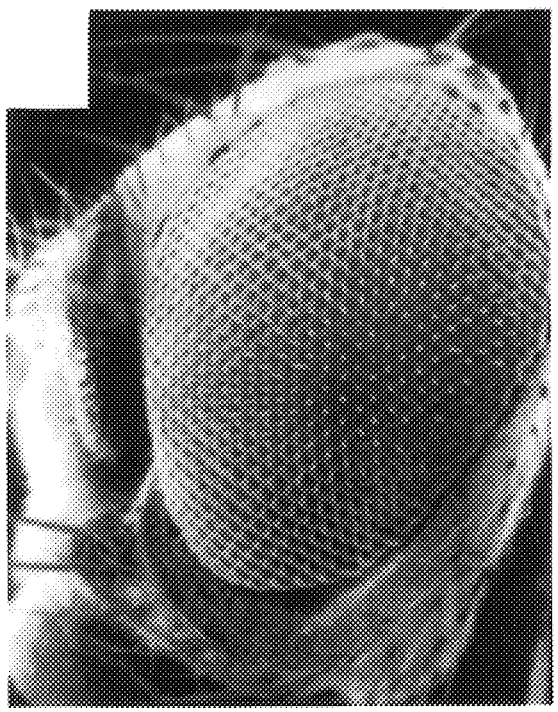
FIG. 1A. Scanning electron micrograph of the compound eye of the parental strain, yw showing normal ommatidia formation.

In the field of pest control a major goal is to control arthropod pests in a profitable, safe manner which does not result in the development of resistance to the control agent by the arthropod. To this end, the development of biocontrol agents which may be used alone or in conjunction with pesticides and are unlikely to persist in the environment when the pest itself is not present are highly desirable. One manner which is expected to achieve these goals is the development of transgenic varieties of pests. When released into the environment these varieties are capable of disseminating throughout a pest population a genotype(s) which produces a phenotype(s) that is adverse to the reproductive capabilities of the pest and prevents the pest population from reaching its economic threshold. An example of a desirable genotype to introduce into a population in order to limit its reproductive success is a genotype that when expressed causes fatal apoptosis. Ideally, the expression of the fatal genotype is triggered by conditions that can either be reliably predicted to occur naturally or can be induced to occur artificially. For example, the present invention provides for the expression of the apoptotic gene, which can be induced to cause death in embryos exposed to certain environmental temperatures when the gene is present in a population and engineered to be under the control of a heat shock promoter. Alternatively, the expression of the gene may be induced by chemical treatment of the crop to yield embryonic apoptosis. A third alternative is that the expression of the apoptotic gene may be induced by a chemical produced in the crop plant, such as gossypol which is specifically produced by the cotton plant, but not produced by other plants which would be present in the surrounding environment and are not harvested as crops. In this case the apoptotic gene would be induced in larvae which have consumed a portion of the plant and these larvae would not survive the molt to the next instar.

The discovery of the genetically distinct gene grim, which defines the third apoptotic function in the H99 genomic interval of *Drosophila melanogaster*, encodes a potent activator of apoptosis and whose expression can be induced, represents a significant advancement for the development of biocontrol agents for arthropods. It is also expected that the discovery of the DNA sequence of grim and the novelty of its amino acid sequence, as compared to other known programmed cell death genes, will have important implications in the development of therapeutic and preventative agents for human diseases which result in the misregulation of apoptotic programming such as AIDS, cancer and neurodegenerative disease. Those skilled in the art will realize that the nucleic and amino acid sequences disclosed will also find utility in a variety of applications in the development of therapeutic and preventative agents for certain human diseases which disrupt normal cell apoptosis. Examples of such applications within the scope of the present invention comprise development of targeting vectors or techniques to allow insertion and expression of the grim gene in cells such as tumor cells and cells infected with HIV.

Several lines of evidence establish that grim encodes an activator of programmed cell death. First, germline transformation of genomic DNA spanning the grim locus resulted in restoration of cell death to H99 mutant embryos. Although only partial rescue of the cell death defect by the grim cosmid was observed, the extent of rescue was dose dependent and similar to levels of rescue obtained by corresponding doses of genomic rpr DNA. Second, the N-terminal portion of GRIM shares conspicuous similarity to RPR, a protein already well established as an activator of cell death in Drosophila [White, et al., 1994; Pronk, et al., 1996; White, et al., 1996]. Third, the induction of grim either in cultured cells or in ectopic tissues triggered extensive cell death that was apoptotic in appearance, prevented by a viral inhibitor of apoptosis and detected by methods that are selective for this form of cell death (acridine orange staining [Abrams, et al., 1993] and TUNEL [Gavrieli, et al., 1992]). These results argue strongly for an apoptotic mode of cell killing induced by grim. Finally, the distribution of grim transcript during embryogenesis is coincident with patterns of embryonic cell death and the inventors occasionally detect compartmentalized signals for grim RNA inside phagocytes. This feature is an unusual staining characteristic that has also been observed with probes for rpr [White, et al., 1994; Zhou, et al., 1995] and hid [Grether, et al., 1995] and probably reflects hybridization to RNAs that persist within engulfed cell corpses. These observations suggest that, like other programmed cell death genes, RNA expressed from the grim gene anticipates the onset of cell death.

The predicted consequences of ectopic grimORF expression strongly suggest that grim activity is mediated by a protein product which provides an associated cell autonomous function. The mechanism by which grim elicits the apoptosis program remains to be determined as does the functional significance of N-terminal motif shared between grim, rpr and hid. In contrast to reported alignments between RPR and some death domain proteins [Cleveland and Ihle, 1995; Golstein, et al., 1995; Golstein, et al., 1995] no similar alignments were detected for GRIM.

Genetics of the H99 cell death interval grim is the third gene mapped thus far to the H99 deletion mutation. While grim clearly meets all requisite criteria for this predicted function, the possibility that additional programmed cell death genes may reside in the H99 interval cannot be excluded. Genetic approaches to this problem are hampered by the fact that only alleles of hid were recovered from very extensive screens for chemically-induced lethal mutations in the H99 interval [Abbot and Lengyel, 1991; White, et al., 1994; Grether, et al., 1995]. These lesions have been carefully examined and, although they do exhibit partial cell death phenotypes, hid mutants are distinctly less severe than the complete apoptotic failure exhibited by H99 [Grether, et al., 1995].

In Drosophila, and in other species, tight linkage can occur among groups of genes that share closely related functions [reviewed in Lawrence, 1992; Krumlauf, 1994]. Typically, the individual members within conserved gene clusters share a common orientation of transcription and a considerable degree of sequence similarity. Therefore, the H99 cell death interval apparently shares some, but not all, of the classic features of a complex: grim, hid and rpr share commonality of orientation and function yet outside a very limited stretch, these proteins share little or no sequence similarity.

Models of apoptosis signaling by grim

The induction of grim was sufficient to trigger apoptosis in embryos that were homozygous for the H99 deletion. This observation rules out an absolute requirement for either rpr or hid during grim mediated cell death. Among a number of inducible transgenes tested thus far [Grether, et al., 1995], only rpr and hid also triggered significant apoptosis in the H99 background. Since co-expression of p35 blocks apoptosis triggered by grim, rpr and hid [Grether, et al., 1995; White, et al., 1996] all three might ultimately activate a common pathway involving conserved ICE/CED-3 like proteases which are targets for inactivation by p35. Moreover, grim induction was able to trigger apoptosis at a time in early development when no such effects were observed with rpr. This distinction could reflect differences in cell death signaling that are uncovered during early development.

Alternatively, two or more entirely parallel pathways, each of which is separately blocked by p35, could define the effector circuits downstream of these genes. The present data do not exclude the possibility that either of the above scenarios may occur. In either scenario, grim, rpr and hid might represent alternate switches or nodes which could be activated by similar yet distinct sets of converging apoptotic signals. Preliminary evidence to support this idea comes from assays that monitor the differential regulation of these gene products in response to stimuli that provoke ectopic cell death.

Biological Functional Equivalents

Modification and changes may be made in the structure of the encoded polypeptides used in the vectors and DNA segments of the present invention and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to the following codon table:

TABLE 1

| Amino Acids | | | Condons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG | CUA | CUC | CUG | CUU |
| Methionine | Met | M | AUG | | | |
| Asparagine | Asn | N | AAC | AAU | | |
| Proline | Pro | P | CCA | CCC | CCG | CCU |
| Glutamine | Gln | Q | CAA | CAG | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU |
| Valine | Val | V | GUA | GUC | GUG | GUU |
| Tryptophan | Trp | W | UGG | | | |
| Tyrosine | Tyr | Y | UAC | UAU | | |

For example, certain amino acids may be substituted for other amino acids in a protein structure without appreciable loss of interactive binding capacity with structures such as, for example, binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the apoptotic proteins, or corresponding DNA sequences which encode said proteins without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. Equally, the same considerations may be employed to create a protein or polypeptide with counterveiling (e.g., antagonistic) properties. It is thus contemplated by the inventors that various changes may be made in the sequence of the GRIM protein or peptide (or underlying DNA) without appreciable loss of biological utility or activity.

Epitopic Core Regions

U.S. Pat. No. 4,554,101 (Hopp, incorporated herein by reference) teaches the identification and preparation of epitopes from primary amino acid sequences on the basis of hydrophilicity. Through the methods disclosed in Hopp one of skill in the art would be able to identify epitopes from within an amino acid sequence such as the GRIM sequence disclosed herein (SEQ ID NO:2). These regions are also referred to as "epitopic core regions".

Numerous scientific publications have been devoted to the prediction of secondary structure, and to the identification of epitopes, from analyses of amino acid sequences (Chou & Fasman, 1974a,b; 1978a,b, 1979). Any of these may be used, if desired, to supplement the teachings of Hopp in U.S. Pat. No. 4,554,101. Moreover, computer programs are currently available to assist with predicting antigenic portions and eptiopic core regions of proteins. Examples include those programs based upon the Jameson-Wolf analysis (Jameson & Wolf, 1998; Wolf et al., 1988), the program PepPlot® (Brutlag et al., 1990; Weinberger et al., 1985), and other new programs for protein tertiary structure prediction (Fetrow & Bryant, 1993).

Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

Use Of Nucleic Acid Segments To Isolate Full Length Genomic Sequences

The nucleic acid sequences of the present invention may be used to isolate the full length genomic sequences encoding the grim gene and surrounding control regions or homologous genes and their surrounding control regions. A genomic library could be constructed by well known techniques such as those taught in Sambrook et al., (1989). For example, genomic DNA may be isolated from *Drosophila melanogaster* tissue and partially digested with a restriction enzyme such as Sau 3A. The digested DNA would then be packaged in a lambda vector by the use, for example, of the Packagene system (Promega). This library could then be screened by transferring the genomic clones to a solid substrate such as a nitrocellulose filter and hybridizing them to labeled nucleic acid sequences of the present invention in order to select for the grim gene or homologous genes, or alternatively, the library could be screened by any one of the methods generally known to those skilled in the art.

It is understood that because of interspecies homology, the nucleic acid segments of the present invention will also be useful to isolate the genomic sequences or even cDNA sequences from other species of animals. The nucleic acid segments of the present invention of any size up to and including the entire sequence designated as SEQ ID NO:1 could be labeled and used as a probe to isolate the genomic sequences, including the intron sequences and control sequences for gene expression of the grim gene or relatively homologous genes. An important use of this sequence information would be to determine whether the grim gene and other programmed cell death genes are controlled by similar promoter/enhancer elements or whether there are tissue specific differences. This would enable the targeting of activators/repressors to specific tissues. The isolation of the promoter regions will also allow the screening of candidate substances as activators or inhibitors of genetic expression of grim and other programmed cell death genes.

In order to identify the desired genomic sequences, the individual clones could be separated, for example by polyacrylamide gel electrophoresis, or agarose gel electrophoresis and then transferred to a filter such as a nitrocellulose filter or any other suitable material. The nucleic acid probe would then be labeled with $^{32}$P by enzymatic labeling with polynucleotide kinase, for example. The clone could also be radioactively labeled by nick translation or in a polymerase chain reaction that included radiolabeled nucleotides. Alternatively, the probe could be labeled with a fluorescent marker or any fluorophore. Such labeling techniques are well known in the art.

The labeled probe would then be hybridized to the denatured DNA on the filter and washed under increasingly stringent conditions, incrementally higher temperatures for example, until the positive clones can be identified by autoradiography or by fluorescence. These positive clones would then be rescreened and sequenced to determine the full gene sequence encoding the GRIM protein or other proteins which have relatively homologous DNA sequences.

The full protein could then be expressed in an *E. coli* strain, for example, and used for further analysis. It is understood that the protein could also be truncated or altered by site directed mutagenesis, for example and that such altered proteins or partial sequences would also fall within the scope of the present invention.

Nucleic Acid Hybridization

The DNA sequences disclosed herein will also find utility as probes or primers in nucleic acid hybridization embodiments. As such, it is contemplated that oligonucleotide fragments corresponding to the sequence of SEQ ID NO:1 for stretches of between about 10 nucleotides to about 20 or to about 30 nucleotides will find particular utility, with even longer sequences, e.g., 40, 50, 100, even up to full length, being more preferred for certain embodiments. The ability of such nucleic acid probes to specifically hybridize to programmed cell death-encoding sequences will enable them to be of use in a variety of embodiments. For example, the probes can be used in a variety of assays for detecting the presence of complementary sequences in a given sample. However, other uses are envisioned, including the use of the sequence information for the preparation of mutant species primers, or primers for use in preparing other genetic constructions.

Nucleic acid molecules having stretches of 10, 20, 30, 50, or even of 100 nucleotides or so, complementary to SEQ ID NO:1 will have utility as hybridization probes. These probes will be useful in a variety of hybridization embodiments, such as Southern and northern blotting in connection with analyzing gene expression or gene regulation in diverse species. The total size of fragment, as well as the size of the complementary stretch(es), will ultimately depend on the intended use or application of the particular nucleic acid segment. Smaller fragments will generally find use in hybridization embodiments, wherein the length of the complementary region may be varied, such as between about 10 and about 100 nucleotides, or even up to full length according to the complementary sequences one wishes to detect.

The use of a hybridization probe of about 9 nucleotides in length allows the formation of a duplex molecule that is both stable and selective. Molecules having complementary sequences over stretches greater than 9 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102 (herein incorporated by reference) or by introducing selected sequences into recombinant vectors for recombinant production.

Accordingly, the nucleotide sequences of the invention may be used for their ability to selectively form duplex molecules with complementary stretches of programmed cell death genes or cDNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt andor high temperature conditions, such as provided by 0.02M–0.15M NaCl at temperatures of 50° C. to 70° C. Such selective conditions tolerate little, if any, mismatch between the probe and the template or target strand, and would be particularly suitable for isolating apoptosis genes possessing significant homology to the grim gene.

It is understood in the art that a nucleic acid sequence will hybridize with a complementary nucleic acid sequence under high stringency conditions even though some mismatches may be present. Such closely matched, but not perfectly complementary sequences are also encompassed by the present invention. For example, differences may occur through genetic code degenerency, or by naturally occurring or man made mutations and such mismatched sequences would still be encompassed by the present claimed invention.

Of course, for some applications, for example, where one desires to prepare mutants employing a mutant primer strand hybridized to an underlying template or where one seeks to isolate GRIM-encoding sequences from related species, functional equivalents, or the like, less stringent hybridization conditions will typically be needed in order to allow formation of the heteroduplex. In these circumstances, one may desire to employ conditions such as 0.1 5M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmentally undesirable reagents. In the case of enzyme tags, colorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

Longer DNA segments will often find particular utility in the recombinant production of peptides or proteins. DNA segments which encode peptide antigens from about 15 to about 50 amino acids in length, or more preferably, from about 15 to about 30 amino acids in length are contemplated to be particularly useful, as are DNA segments encoding entire GRIM proteins. DNA segments encoding peptides will generally have a minimum coding length in the order of about 45 to about 150, or to about 90 nucleotides. DNA segments encoding full length proteins may have a minimum coding length in the order of about 414 nucleotides for a protein in accordance with SEQ ID NO:2.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol. For example, nucleic acid fragments may be prepared in accordance with the present invention which are up to 10,000 base pairs in length, with segments of 5,000 or 3,000 being preferred and segments of about 1,000 base pairs in length being particularly preferred.

It will be understood that this invention is not limited to the particular nucleic acid and amino acid sequences of SEQ ID NO:1 and SEQ ID NO:2. Therefore, DNA segments prepared in accordance with the present invention may also encode biologically functional equivalent proteins or peptides which have variant amino acids sequences. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged.

Recombinant Host Cells, Vectors and their Promoters/Enhancers

As used herein, the term "engineered" or "recombinant" cell is intended to refer to a cell into which a recombinant gene, such as a gene encoding the GRIM protein has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator proteins. At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV 40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between elements is flexible, so that promoter function is preserved when elements are inverted or moved relative to one another. In the tk promoter, the spacing between elements can be increased to 50 bp apart before activity begins to decline. Depending on the promoter, it appears that individual elements can function either cooperatively or independently to activate transcription.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Aside from this operational distinction, enhancers and promoters are very similar entities. They have the same general function of activating transcription in the cell. They are often overlapping and contiguous, often seeming to have a very similar modular organization. Taken together, these considerations suggest that enhancers and promoters are homologous entities and that the transcriptional activator proteins bound to these sequences may interact with the cellular transcriptional machinery in fundamentally the same way.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventor does not exclude the possibility of employing a genomic version of a particular gene where desired.

The engineering of DNA segment(s) for expression in a prokaryotic or eukaryotic system may be performed by techniques generally known to those of skill in recombinant expression. It is believed that virtually any expression system may be employed in the expression of the apoptotic gene grim. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species (Bolivar et al., 1977). pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as E. coli LE392.

Those promoters most commonly used in recombinant DNA construction include the B-lactamase (penicillinase) and lactose promoter systems (Chang et al, 1978; Itakura et al., 1977; Goeddel et al., 1979) and a tryptophan (trp) promoter system (Goeddel et al., 1980; EPO Appl. Publ. No. 0036776). While these are the most commonly used, other microbial promoters have been discovered and utilized, and details concerning their nucleotide sequences have been published, enabling a skilled worker to ligate them functionally with plasmid vectors (EPO Appl. Publ. No. 0036776).

In addition to prokaryotes, eukaryotic microbes, such as yeast cultures may also be used. Saccharomyces cerevisiae, or common baker's yeast is the most commonly used among eukaryotic microorganisms, although a number of other strains are commonly available. For expression in Saccharomyces, the plasmid YRp7, for example, is commonly used (Stinchcomb et al., 1979; Kingsman et al., 1979; Tschemper et al., 1980). This plasmid already contains the trpl gene which provides a selection marker for a mutant strain of yeast lacking the ability to grow in tryptophan, for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, an origin of replication, and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (Tissue Culture, 1973). Examples of such useful host cell lines are VERO and HeLa cells, Chinese hamster ovary (CHO) cell lines, and W138, BHK, COS-7, 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

How to Use Promoters in Gene Expression Assays

There are two basic procedures for studying the in vivo expression of cloned genes and their promoters. In transient systems, the gene of interest (grim) is introduced into a population of cultured cells, and its activity is assayed within a few hours to a few days. The original transient expression experiments utilized encapsidated SV40 recombinants. Although only a small fraction of the cells take up and express the recombinant genes, transcription of the foreign gene can be readily detected. Alternatively, if the promoter (control region) of the recombinant gene is under study, the promoter and enhancer can be cloned with the coding region of a gene such as Herpes Simplex thymidine kinase (tk) or E. Coli chloramphenicol acetyltransferase (CAT). The activity of the promoter can be monitored by an assay for the presence of the appropriate gene product.

The second method for studying cloned genes and their control regions is stable transfection. Stable transfection is the preferred method for obtaining moderate expression levels from a transfected gene in a long term continuous culture. In this method the recombinant DNA molecule (grim+promoter/enhancer combination) is introduced by DNA-mediated gene transfer techniques into cultured cells. Identification of the recombinant stable transfectant among the population of untransformed cells requires a change in phenotype. Usually the inclusion of a drug selection marker aids in the discovery and selection of the stable transformants. Plasmids that are suitable for subcloning an expression cassette containing the grim sequence and any of the promoter/enhancer combinations listed below are well known to those of skill in the art. Such plasmids containing the grim sequence and promoter/enhancer can be used in a stable transfection protocol or transient transfection procedure.

Below are lists of viral promoters, cellular promoters/enhancers and inducible promoters/enhancers that could be used in combination with the Grim construct. Additionally any promoter/enhancer combination (AS PER the Eukaryotic Promoter Data Base EPDB) could also be used to drive expression of the Grim transgene in a Gene Therapy protocol.

TABLE 2

| ENHANCER | REFERENCES |
|---|---|
| Immunoglobulin Heavy Chain | Hanerji et al., 1983; Gilles et al., 1983; Grosschedl and Baltimore, 1985; Atchinson and Perry, 1986, 1987; Imler et al., 1987; Weinberger et al., 1988; Kiledjian et al., 1988; Porton et al., 1990 |
| Immunoglobulin Light Chain | Queen and Baltimore, 1983; Picard and Schafffner, 1984 |
| T-Cell Receptor | Luria et al., 1987, Winoto and Baltimore, 1989; Redondo et al., 1990 |
| HLA DQ a and DQ B | Sullivan and Peterlin, 1987 |
| β-Interferon | Goodbourn et al., 1986; Fujita et al., 1987; Goodbourn and Maniatis, 1985 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al., 1989 |
| Muscle Creatine Kinase | Jaynes et al., 1988; Horlick and Benfield, 1989; Johnson et al., 1989a |
| Prealbumin (Transthyretin) | Costa et al., 1988 |
| Elastase I | Omitz et al., 1987 |
| Metallothionein | Karin et al., 1987; Culotta and Hamer, 1989 |
| Collagenase | Pinkert et al., 1987; Angel et al., 1987 |
| Albumin Gene | Pinkert et al., 1987, Tronche et al., 1989, 1990 |
| a-Fetoprotein | Godbout et al., 1988; Campere and Tilghman, 1989 |
| t-Globin | Bodine and Ley, 1987; Perez-Stable and Constantini; 1990 |
| β-Globin | Trudel and Constantini, 1987 |
| e-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| $a_{1\text{-Antitrypain}}$ | Latimer et al., 1990 |
| H2B (TH2B) Histone | Hwang et al., 1990 |
| Mouse or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Duchenne Muscular Dystrophy | Klamut et al., 1990 |
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987 Schaffner et al., 1988 |
| Polyoma | Swartzendruber and Lehman, 1975; Vasseur et al., 1980; Katinka et al., 1980, 1981; Tyndell et al., 1981; Dandolo et al., 1983; deVilliers et al., 1984; Hen et al., 1986; Satake et al., 1988; Campbell and Villarreal, 1988 |
| Retroviruses | Kriegler and Botchan, 1982, 1983; Levinson et al., 1982; Kriegler et al., 1983, 1984a,b, 1988; Bosze et al., 1986; Miksicek et al., 1986; Celander and Haseltine, 1987; Thiesen et al., 1988; Celander et al., 1988; Chol et al., 1988; Reisman and Rotter, 1989 |
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al., 1987; Stephens and Hentschel, 1987; Glue et al., 1988 |
| Hepatitis B Virus | Bulla and Siddiqui, 1986; Jameel and Siddiqui, 1986; Shaul and Ben-Levy, 1987; Spandau and Lee, 1988; Vannice and Levinson, 1988 |
| Human Immunodeficiency | Muesing et al., 1987; Hauber and Cullan, 1988; Jakobovits et al., |

TABLE 2-continued

| ENHANCER | REFERENCES |
| --- | --- |
| Virus | 1988; Feng and Holland, 1988; Takebe et al., 1988; Rowen et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukemia Virus | Holbrook et al., 1987; Quinn et al., 1989 |

TABLE 3

| Element | Inducer | References |
| --- | --- | --- |
| MT II | Phorbol Ester (TFA)<br>Heavy metals | Palmiter et al., 1982; Haslinger and Karin, 1985; Searle et al., 1985; Stuart et al., 1985; Imagawa et al., 1987; Karin ®, 1987; Angel et al., 1987b; McNeall et al., 1989 |
| MMTV (mouse mammary tumor virus) | Glucocorticoids | Huang al., 1981; Lee et al., 1981; Majors and Varmnnus, 1983; Chandler et al.; 1983; Lee et al., 1984; Fonta et al., 1985; Sakai et al., 1986 |
| β-Interferon | poly(rI)X<br>poly(rc) | Tavernier et al., 1983 |
| Adenovirus 5 E2 | Ela | Imperiale and Nevins, 1984 |
| Collagenase | Phorbol Ester (TPA) | Angle et al., 1987a |
| Stromelysin | Phorbol Ester (TPA) | Angle et al., 1987b |
| SV40 | Phorbol Ester (TFA) | Angel et al., 1987b |
| Murine MX Gene | Interferon, Newcastle Disease Virus | |
| GRP78 Gene | A23187 | Resendez et al., 1988 |
| a-2-Macroglobulin | IL-6 | Kunz et al., 1989 |
| Vimentin | Serum | Rittling et al., 1989 |
| MHC Class I Gene H-2kb | Interferon | Blanar et al., 1989 |
| HSP70 | Ela, SV40 Large T Antigen<br>Heat Shock | Taylor et al., 1989; Taylor and Kingston, 1990a,b |
| Proliferin | Phorbol Ester-TPA | Mordacq and Linzer, 1989 |
| Tumor Necrosis Factor | FMA | Hensel et al., 1989 |
| Thyroid Stimulating Hormone a Gene | Thyroid Hormone | Chatterjee et al., 1989 |

Immunodetection Methods

In still further embodiments, the present invention concerns immunodetection methods for binding, purifying, removing, quantifying or otherwise generally detecting apoptotic activity. The apoptotic protein of the present invention may be employed to detect antibodies having reactivity therewith, or, alternatively, antibodies prepared in accordance with the present invention, may be employed to detect other apoptotic proteins or peptides. The steps of various useful immunodetection methods have been described in the scientific literature, such as, e.g., Nakamura et al.(1987), incorporated herein by reference.

In general, the immunobinding methods include obtaining a sample suspected of containing an apoptotic protein, peptide or anti-apoptotic antibody, and contacting the sample with an antibody or apoptotic protein or peptide in accordance with the present invention, as the case may be, under conditions effective to allow the formation of immunocomplexes.

These methods include methods for removing undesirable components from a given sample. In these instances, an antibody will most likely be used to remove an antigenic component from a sample. The antibody will preferably be linked to a solid support, such as in the form of a column matrix, and the sample suspected of containing the unwanted antigenic component will be applied to the immobilized antibody. A purged or purified sample may be obtained free from the unwanted antigen simply by collecting the sample from the column and leaving the antigen immunocomplexed to the immobilized antibody.

In terms of antigen detection, the biological sample analyzed may be any sample that is suspected of containing a GRIM-specific antigen, such as an embryo, a tissue section or a homogenized embryo or tissue extract, an embryonic cell, an embryonic cell membrane preparation, separated or purified forms of any of the above protein-containing compositions, or even any biological fluid that comes into contact with aforementioned tissues.

Contacting the chosen biological sample with the protein, peptide or antibody under conditions effective and for a period of time sufficient to allow the formation of immune complexes (primary immune complexes) is generally a matter of simply adding the composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of the radioactive, fluorescent, biological or enzymatic tags or labels well known to those skilled in the art. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The apoptotic protein, peptide or antibody employed in the detection may itself be linked to a detectable label, wherein one would then simply detect this label, thereby allowing the amount of the primary immune complexes in the composition to be determined.

Alternatively, the first added component that becomes bound within the primary immune complexes may be detected by means of a second binding ligand that has binding affinity for the primary antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the primary antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

Monoclonal Antibody Generation

Means for preparing and characterizing antibodies are well known in the art (See, e.g., Antibodies: A Laboratory Manual, Cold Spring Harbor Laboratory, 1988; incorporated herein by reference).

The methods for generating monoclonal antibodies (MAbs) generally begin along the same lines as those for preparing polyclonal antibodies. Briefly, a polyclonal antibody is prepared by immunizing an animal with an immunogenic composition in accordance with the present invention (either with or without prior immunotolerizing, depending on the antigen composition and protocol being employed) and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimide and bis-diazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal can be bled and the serum isolated and stored, and/or the animal can be used to generate MAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified apoptotic protein, polypeptide or peptide (or any protein complex, such as a fusion protein containing an immunologically active portion of the apoptotic protein GRIM, if used after tolerization to common antigens). The immunizing composition is administered in a manner effective to stimulate antibody producing cells. Rodents such as mice and rats are preferred animals, however, the use of rabbit, sheep or frog cells is also possible. The use of rats may provide certain advantages (Goding, 1986, pp. 60–61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter el al.(1977). The use of electrically induced fusion methods is also appropriate (Goding pp. 71–74, 1986).

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

DNA Delivery

Following the generation of recipient cells, it is envisioned that the present invention may generally next be used to direct the introduction an exogenous DNA segment, such as a cDNA or gene, into a recipient cell to create a transformed cell. The frequency of occurrence of cells receiving DNA is believed to be low. Moreover, it is most likely that not all recipient cells receiving DNA segments will result in a transformed cell wherein the DNA is stably integrated into the animal genome and/or expressed. Some may show only initial and transient gene expression. However, certain eukaryotic cells may be stably transformed, and these cells developed into transgenic animals, or arthropods, preferably insects or mites, through the application of the techniques disclosed herein.

There are many methods for introducing transforming DNA segments into cells, but not all are suitable for delivering DNA to eukaryotic cells. Suitable methods are believed to include virtually any method by which DNA can be introduced into a cell, such as by direct delivery of DNA, by desiccation/inhibition-mediated DNA uptake, by electroporation, by agitation with silicon carbide fibers, by acceleration of DNA coated particles, by chemical transfection, by lipofection or liposome-mediated transfection, by calcium chloride-mediated DNA uptake, etc. In certain embodiments, acceleration methods are preferred and include, for example, microprojectile bombardment and the like.

A. Electroporation

Where one wishes to introduce DNA by means of electroporation, it is contemplated that the method of Krzyzek et al.(U.S. Ser. No. 07/635,279 filed Dec. 28, 1990, incorporated herein by reference) will be particularly advantageous. In this method, certain cell wall-degrading enzymes, such as pectin-degrading enzymes, are employed to render the target recipient cells more susceptible to transformation by electroporation than untreated cells. Alternatively, recipient cells are made more susceptible to transformation, by mechanical wounding.

To effect transformation by electroporation one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding in a controlled manner. Such cells would then be recipient to DNA transfer by electroporation, which may be carried out at this stage, and transformed cells then identified by a suitable selection or screening protocol dependent on the nature of the newly incorporated DNA.

B. Microprojectile Bombardment

A further advantageous method for delivering transforming DNA segments to cells is microprojectile bombardment. In this method, particles may be coated with nucleic acids and delivered into cells by a propelling force. Exemplary particles include those comprised of tungsten, gold, platinum, and the like.

For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Results from such small scale optimization studies are disclosed herein and the execution of other routine adjustments will be known to those of skill in the art in light of the present disclosure.

Marker Genes

In order to improve the ability to identify transformants, one may desire to employ a selectable or screenable marker gene as, or in addition to, the expressible gene of interest. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., $\alpha$-amylase, $\beta$-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell membrane, and which protein includes a unique epitope is considered to be particularly advantageous. Such a secreted antigen marker would ideally employ an epitope sequence that would provide low background in transformants, a promoter-leader sequence that would impart efficient expression and targeting across the plasma membrane, and would produce protein that is bound in the cell membrane and yet accessible to antibodies. A normally secreted protein modified to include a unique epitope would satisfy all such requirements.

Virtually any detectable epitope may be employed in such embodiments, as selected from the extremely wide variety of antigen:antibody combinations known to those of skill in the art. The unique extracellular epitope, whether derived from IL-1-$\beta$ or any other protein or epitopic substance, can then be straightforwardly detected using antibody labeling in conjunction with chromogenic or fluorescent adjuncts. Numerous other possible selectable and/or screenable marker genes will be apparent to those of skill in the art. Therefore, it will be understood that the following discussion is exemplary rather than exhaustive. In light of the techniques disclosed herein and the general recombinant techniques which are known in the art, the present invention renders possible the introduction of any gene, including marker genes, into a recipient cell to generate a transformant.

Selectable Markers

Possible selectable markers for use in connection with the present invention include, but are not limited to, a neo gene (Potrykus el al., 1985) which codes for kanamycin resistance and can be selected for using kanamycin, G418, etc.; a bar gene which codes for bialaphos resistance; a mutant aroA gene which encodes an altered EPSP synthase protein (Hinchee et al., 1988) thus conferring glyphosate resistance; a nitrilase gene such as bxn from *Klebsiella ozaenae* which confers resistance to bromoxynil (Stalker el al., 1988); a mutant acetolactate synthase gene (ALS) which confers resistance to imidazolinone, sulfonylurea or other ALS inhibiting chemicals (European Patent Application 154,204, 1985); a methotrexate resistant DHFR gene (Thillet et al., 1988), or a mutated anthranilate synthase gene that confers resistance to 5-methyl tryptophan.

It is also contemplated that a negative selection could be necessary in order to screen a population of transformants for rare homologous recombinants generated through gene targeting. For example, a homologous recombinant may be identified through the inactivation of a gene that was previously expressed in that cell. It is contemplated that negative selectable markers may also be useful in other ways. One application is to construct transgenic lines in which one could select for transposition to unlinked sites. In the process of tagging it is most common for the transposable element to move to a genetically linked site on the same chromosome. A selectable marker for recovery of rare transformants in which transposition has occurred to an unlinked locus would be useful. For example, the enzyme cytosine deaminase may be useful for this purpose (Stouggard, J., 1993). In the presence of this enzyme the compound 5-fluorocytosine is converted to 5-fluorouracil which is toxic to animal cells. If a transposable element is linked to the gene for the enzyme cytosine deaminase, one may select for transposition to unlinked sites by selecting for transposition events in which the resultant transformant is now resistant to 5-fluorocytosine. The parental cells containing transpositions to linked sites will remain sensitive to 5-fluorocytosine. Resistance to 5-fluorocytosine is due to loss of the cytosine deaminase gene through genetic segregation of the transposable element and the cytosine deaminase gene.

Methodology

Drosophila stocks

Df(3L)H99, In(3L)hid$^{WR+X1}$, were as previously described by Abbot and Lengyel [1991]. Isolation of X14 and X25 was as described by Grether [1994] and White, et al.[1994] and hsrpr46A and hsrpr53 were as described by White, et al.[1996]. GMR-p35 was as described by Hay, et al.[1994]. The wild type strain used was Canton S and the parental strain for germline transformations was yw$^{67c}$23. All genetic symbols are according to Lindsley and Zimm [1992].

Cosmid transformation and phenotypic analysis

A cosmid from a genomic walk [Grether, 1994; White, et al., 1994] was determined to span the grim gene. A mixture of 437 µg/ml cosmid DNA and 100 µg/ml Δ2–3 helper plasmid DNA was injected into several thousand yw embryos [Rubin and Spradling, 1982]. Four independent transformed lines were isolated. Two of these map to the third chromosome (grim-CosB and grim-CosD) one maps to the second (grim-CosA) and one is on the X (grim-CosC). Two of these (lines A and C) were introduced into the H99 background and a recombinant of grim-CosD was constructed to obtain w; grim-CosD, H99 ri,p/TM3, Sb flies. Levels of rescue by grim cosmid, were determined by staining with acridine orange [Abrams, et al., 1993] and found to be similar among the three lines A, C and D. To construct a line with four grim transgenes in the H99 background, homozygous grim-CosA flies were mated with w; CyO/+; grim-CosD, H99 ri,p/TM3 Sb rip individuals. CyO, Sb virgins, and male CyO; grim-CosD, H99, ri,p progeny were mated and in the following generation, individuals of the grim-CosA; grim-CosD H99,ri,p/TM3, Sb rip genotype were selected by eye color and ri.

Isolation, characterization and sequencing of grim cDNA

A 3 kb Hpa1/Not1 fragment from the grim cosmid was used to screen an embryonic cDNA library in λgt10 [Poole, et al., 1985]. Eight clones with similar sized inserts were isolated from ~500,000 clones screened. One of these, clone A, was confirmed to map to the H99 interval by Southern hybridization to both wild type DNA and DNA isolated from H99 embryos. The clone A insert was subcloned into the EcoRI site of pBluescript SK+ and sequenced by dideoxy-DNA sequencing using the Sequenase 2.0 DNA Sequencing Kit (United States Biochemical, Cleveland, Ohio.) as recommended by the manufacturer and $^{35}$S-dATP (Amersham, Arlington Heights, Ill.).

Southerns and Northerns

Genomic DNA from adult flies was isolated according to the procedure of Ashburner [1989]. To isolate DNA from homozygous H99 embryos, samples were aged so that all embryos were older than ~18 hrs and dechorionated before sorting. At this stage and beyond, mutants can be readily identified by virtue of their head defect and inability to hatch. DNA was isolated from ~300–600 embryos as in Ashburner [1989] except that the phenol:chloroform extraction was omitted and the DNA was precipitated with a 0.5 volume of isopropanol. DNA from ~100 sorted H99 embryos per lane were typically used for Southern hybridizations [Sambrook, et al., 1989]. As expected, probes mapping inside the H99 interval fail to produce hybridizing signals on H99 DNA whereas probes outside the interval do. RNA was isolated from 7–12 hour embryos in a procedure similar to that of Chirgwin, et al.[1979] and was processed for northern hybridizations as described by Sambrook, et al.[1989].

Histological methods

Acridine orange staining was performed as described by Abrams, et al.[1993]. Embryos were staged according to Campos-Ortega and Hartenstein [1985]. TUNEL [Gavrieli, et al., 1992] was performed as previously described by White, et al.[1994]. A grim RNA probe for use in whole-mount in situ hybridizations [Tautz and Pfeifle, 1989] was transcribed from the linearized cDNA using the DIG RNA labeling kit (Boeringer Mannheim, Indianapolis, Ind.). Hybridizations were performed on 0–16 hour embryos from yw and H99/TM3 stocks. No signal was detected in H99 homozygotes. In(3L)hid$^{WR+X1}$ embryos were also examined with the grim probe and identified by their head involution defect [Abbot and Lengyel, 1991]. To look for possible cross regulation between grim and rpr, heat shocked HS-grim2.1 embryos were hybridized with a rpr probe [White, et al., 1994], and heated hsrpr46A embryos were hybridized with the grim probe.

Construction of HS-grim transgenic strains and phenotypic analysis

An EcoRi fragment containing grim cDNA was inserted in the sense orientation into the pCaSpeR/hsp70 vector [Grether, et al., 1995] to generate the HS-grim plasmid. A mixture of 500 µg/ml HS-grim DNA and 100 µg/ml Δ2–3 helper plasmid DNA was injected into yw embryos. Two independent transformants (from a total of seven isolated) were mapped and examined in detail. For heat shock treatment, embryos from homozygous strains were collected at 25° C., aged at 18° C., heat treated in a 39° C. water bath for 30 minutes, and then allowed to recover at 25° C. for 1 hour. Subsequently, the samples were processed for either acridine orange staining, TUNEL labeling or in situ hybridization. Embryos from flies of homozygous HS-grim2.1, HS-grim3 and HS-grim2.1; H99/TM3 Sb were checked for grim-induced cell killing. Embryos from untransformed yw and H99/TM3 Sb flies were also subjected to the same heat shock treatment as a control. For comparisons to rpr-induced cell death, homozygous hsrpr46A and hsrpr53A [White, et al., 1996] embryos were treated in parallel. To determine lethality, known numbers of 0–8 hr homozygous embryos were heat treated and empty egg cases were counted after 24 hr at 25° C. The results described are the combined results of 2 separate trials in which a total of 197 HS-grim embryos and 187 yw embryos were treated in parallel.

Construction of pGMR-grim transgenic strains and phenotypic analysis

An EcoRI fragment containing grim cDNA was cloned into the pGMR vector [Hay, et al., 1994] in the sense orientation to generate the pGMR-grim transgene. This plasmid was injected into yw embryos at 500 µg/ml, together with the Δ2–3 transposase helper plasmid at 100 µg/ml to produce transgenic flies as described. Seven out of eight independent lines isolated had rough eyes that were substantially reduced in size, a phenotype consistent with increased cell death in the developing eye. One strain, pGMR-grim1, maps to the 2nd chromosome and shows a representative phenotype which is more severe when homozygous. This strain was mated to pGMR-p35 [Hay, et al., 1994] to generate flies homozygous for pGMR-grim1 and pGMR-p35. For scanning electron microscopy, samples were coated with gold-palladium and examined in a JEOL 120 KV electron microscope.

Construction of pMT-grim, pMT-grimORF, cell culture, transfection and cell death assays pMT-grim was made by inserting an 1.1 kb EcoRI-RsaI fragment of grim cDNA into EcoRI-BamHI/Blunt digested pRmHa.3 vector [Bunch, et al., 1988]. The large EcoRI-NcoI fragment of pMT-grim was blunted using Klenow Fragment, and circularized to generate pMT-grimORF which includes the hypothetical start codon through 429 bases downstream of the stop codon. Stably transfected cell lines were produced by cotransfection of 2 $\mu$g of test plasmid with 0.2 $\mu$g pCohygro [Van der Straten, et al., 1989] into $1 \times 10^6$ Schneider L2 cells [Schneider, 1972] cultured in Sf900 II SFM (Gibco BRL, Gaithersburg, Md.) with 50 $\mu$g/ml Gentamicin (Sigma, St. Louis, Mo.). After transfections with pMT-grim or pMT-grimORF DNA alone, or in combination with a similar amount of pMT-p35 plasmid cells were selected with a supplement of 300 $\mu$g/ml hygromycin (Sigma). For induction of the metallothionein responsive promoter, cells were exposed to 700 mM $CuSO_4$.

For transient transfections, SL2 cells were plated at a density of $1 \times 10^6$ cells/well in 6-well plates. Transfections were done with CellFECTIN (Gibco BRL) according to manufacturer's instruction. 48 hours after transfection, cells from each well were split into two wells, and copper was added to one of the two wells. Two procedures were used to measure apoptosis frequency after gene induction in transiently transfected cells. One measure relies upon the appearance of hypodiploid nuclei in flow cytometric assays [Tounekti, et al., 1995] of propidium iodide stained cells. After various treatments, cells were washed off the plates, fixed with 2% formaldehyde in PBS for 15 minutes, stained with 50 $\mu$g/ml propidium iodide in the dark at 4° C., and analyzed within 24 hr on a Becton Dickinson FACScan flow cytometer. The alternative method relies upon loss of co-transfected reporter gene activity to measure apoptosis [Hsu, et al., 1995]. 0.2 $\mu$g of the reporter plasmid (pActin-LacZ) was cotransfected with 2 $\mu$g test plasmids. Forty eight hours later samples were induced and, after another 16 hours, β-galactosidase activity was visualized by fixing cells for 30 minutes with 2% formaldehyde and staining with X-Gal as described by Hsu, el al.[1995].

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Identification and molecular characterization of grim

To test for possible cell death functions in the interval between the proximal break points of DfX14 and DfX25, the inventors produced four independent germline transformants with a cosmid clone that spans the appropriate region. Three of these were tested in a homozygous H99 background for restoration of embryonic cell death by acridine orange staining [Abrams, et al., 1993]. Investigation found that substantial numbers of apoptotic cell deaths are restored to virtually all mutant embryos bearing four doses of the grim cosmid. All three transformant lines examined showed similar levels of rescue and this activity was dose dependent since four doses of the cosmid showed more rescue than two doses. Note that these cell deaths occur in the absence of two other cell death genes in the H99 region, rpr and hid. The partial nature of this phenotypic rescue was reminiscent of the behavior of H99 transformants bearing a rpr cosmid. Therefore apoptotic cells in H99 embryos bearing similar doses of the rpr transgene or the grim transgene were counted. Because they are only partially rescued for cell death, and are still defective for head involution, embryos with these genotypes are easily identified. In these studies, the extent of rescue conferred by four doses of grim was indistinguishable from four doses of rpr. It is noteworthy that artifactual explanations for the restoration of programmed cell death can be eliminated because other transgenes, including at least one cosmid, did not rescue apoptosis in H99 embryos [White, et al., 1994; Grether, et al., 1995].

One transcription unit that mapped to a single ~3 kb Hpa1/Not1 fragment within this cosmid clone at a position that lies ~20 kb distal to the proximal breakpoint of X25 was identified. This fragment was used to isolate eight hybridizing clones from an embryonic cDNA library. These all contained inserts of ~1.6 kb and the clone selected for sequence analysis (clone A) included an extensive poly-A tail. By virtue of its proximity to rpr and its potent cell killing activity the name grim was assigned to this gene.

grim cDNA detected a single 1.6 kb transcript by northern blot analysis of embryonic RNA and, as expected, also recognized a ~5 kb EcoR1 genomic band that is present in wild type flies, but absent in homozygous H99 embryos. These data confirmed that the cDNA clones correspond to expressed sequences from within the H99 interval. Using polymerase chain reaction (PCR) analyses of genomic DNA and partial sequencing of the grim cosmid, no apparent intronic sequences were found. By mapping the cDNA clone onto the cosmid, it was determined that grim is transcribed towards the telomere in an orientation that parallels the direction of rpr and hid expression.

The complete sequence of grim cDNA clone A was determined (SEQ ID NO:1) and confirmed by sequencing genomic-derived PCR products and parts of the grim cosmid. The longest deduced open reading frame (ORF) in the 5'-3' direction is a protein of 138 amino acids, SEQ ID NO:2, which was validated in tests for apoptosis functions (Table 4). The predicted GRIM protein has an estimated pI of 5.8, no helical trans-membrane domains [Rost and Sander, 1994] and shares no significant homology to any sequence in the database as analyzed using BLAST [Altschul, et al., 1990]. However, direct inspection shows that the amino terminal end of this predicted protein shares very notable similarity to RPR and less similarity to HID. Ten of the first fourteen residues of GRIM are identical to the corresponding position in RPR while three of the remainder are conserved substitutions. This region of RPR also shares notable but less similarity to the HID protein [Grether, et al., 1995]. A three way comparison within this region suggests that RPR and GRIM share the most similarity to each other while GRIM and HID share the least.

TABLE 4

Cell Death Induced by Grim*

| Copper treatment | Blue cells per field | | | | | |
|---|---|---|---|---|---|---|
| | Actin-LacZ | pRmHa.3 | HA-hook | grim | grimORF | grim/p35 |
| No | 150 ± 9 | 150 ± 13 | 138 ± 9 | 147 ± 5 | 160 ± 16 | 141 ± 6 |
| Yes | 141 ± 7 | 162 ± 15 | 148 ± 12 | 39 ± 6 | 31 ± 5 | 135 ± 5 |

*Drosophila SL2 cells were transiently transfected with pActin-LacZ (0.2 µg) alone, or cotransfected with pActin-LacZ (0.2 µg) plus empty vector pRmHa.3 (2 µg), pMT-HA-hook (2 µg), pMT-grim (2 µg), pMT-grimORF (2 µg), or pMT-grim and pMT-p35 (2 and 3 µg, respectively). Cells from each well were split to two wells 48 hours after transfection, and copper was added to one of the wells. Cells were fixed and stained with X-gal 16 hours later as described in the methodology herein. β-galactosidase activity data are presented as average number of β-gal-positive (blue) cells (± standard deviation) per field (10× lens) for at least three fields from each of three independent transfections.

EXAMPLE 2

Embryonic expression of grim RNA resembles the embryonic apoptosis pattern grim expression during embryonic development was examined using in situ hybridization with a digoxigenin-labeled RNA probe. The overall distribution of grim RNA distinctly resembled patterns of embryonic apoptosis. At each stage of embryogenesis, grim RNA is present in regions and tissues where cell death occurs. The onset of grim expression occurred in stage 11 embryos (initiation of extensive apoptosis occurs in stage 12). No hybridization was detected in H99 embryos. The gross patterns of grim expression were similar to patterns observed for rpr and hid. A notable exception, however, is that hid expression does not correlate with apoptosis in the embryonic nerve cord at stage 16 [Grether, et al., 1995] whereas signals for both grim and rpr [White, et al., 1994] are clearly found in this location.

A hybridization signal for grim RNA that was subcellularly localized inside some, but not all, macrophages was also detected [Abrams, et al., 1992; Abrams, et al., 1993]. This distribution, also found with probes for rpr [White, et al., 1994; Zhou, et al., 1995] and hid RNAs [Grether, et al., 1995], probably reflects hybridization to mRNAs inside corpses that have recently been engulfed by phagocytic cells and may be characteristic of cell death activators mapping to 75C 1,2 in Drosophila.

EXAMPLE 3 grim is sufficient to induce cell death that can be blocked by co-expression of the anti-apoptotic protein p35

Figure 1B:
FIG. 1B. Scanning electron micrograph of the compound eye of the pGMR-grim1/pGMR-grim1 fly. Two copies of the pGMR-grim1 transgene causes a complete elimination of ommatidia with only a few bristles remaining. Seven of eight independent transformants had this phenotype.

To determine whether grim encodes apoptotic activity, the consequences of ectopic grim expression in a variety of experimental contexts was examined. A grim cDNA was cloned into the pGMR vector (pGMR-grim) that directs specific expression to the developing eye [Hay, et al., 1994] and this construct was used to isolate a total of eight independent germline transformants. As homozygotes, seven of these exhibit the severe eye-ablation phenotype illustrated in FIG. 1B whereas one strain showed no obvious effects. Heterozygotes for the GMR-grim trangene exhibit varying degrees of intermediate phenotypes with eyes that are substantially smaller than wild type and display a characteristic rough appearance.

Whether this eye-ablation phenotype could be affected by the anti-apoptotic protein, p35, a Baculovirus protein that functions to block cell death by inactivating proteases of the ICE/CED-3 family [Clem, et al., 1991; Miura, et al., 1993; Clem and Miller, 1994; Bump, et al., 1995; Xue and Horvitz, 1995] was also tested. To examine this question, strains that simultaneously express both grim and p35 transgenes [Hay, et al., 1994] in the developing eye were produced. The eyes of these co-expressing flies were restored to a wild type size and normal organization. Thus, p35 can suppress the retinal cell death phenotype associated with ectopic grim expression.

In addition the consequence of grim expression in cultured cells was examined. Drosophila SL2 cells [Schneider, 1972] were transfected with pMT-grim, a plasmid designed to conditionally express the grim cDNA from an upstream metal-inducible promoter [Bunch, et al., 1988; Kovach, et al., 1992]. In both transient assays and in stably transfected populations, potent cell killing associated with grim induction was observed. Within four hours of metal treatment, considerable numbers of apoptotic figures can be found in cultures transfected with pMT-grim and by nine hours apoptotic death is very extensive. This effect is indistinguishable from cultures in which rpr has been similarly induced and is not observed in controls.

Two independent methods were used to measure apoptosis. In one, flow cytometry assays that rely upon the appearance of "hypodiploid nuclei" in samples stained with propidium iodide were used. In cultured cells, the appearance of nuclei with a "sub-G1" DNA content is a characteristic determinant of apoptosis and can be used to assess the extent of apoptotic death [Tounekti, et al., 1995]. In transiently transfected samples, a substantial fraction of pMT-grim cells underwent apoptosis after sixteen hours of metal treatment whereas only background levels of cell death occurred in the absence of copper or in control cells which were transfected either with empty vector or an irrelevant protein expressed from the same vector (pMT-HA-hook) [Kramer and Phistry, 1996].

These findings were corroborated with an alternative assay for cell killing which also detects rpr-induced apoptosis and relies upon the loss of co-transfected reporter activity after induction of the test plasmid [Hsu, et al., 1995]. In this case, the number of cells positive for a co-transfected Actin promoter-driven LacZ reporter, pAct-LacZ, was determined sixteen hours after induction (64 hours after transfection). Treatment with metals alone had no effect on the number of LacZ positive cells nor did controls with empty vector or an irrelevant protein (Table 4). In contrast, a drastic reduction of B-galactosidase expressing cells occurred in metal treated cells that had been transfected with pMT-grim and many of the remaining lacZ positive cells in the grim-induced cultures exhibited classic apoptotic morphology. These data indicate that the grim gene product is a potent activator of apoptosis. To confirm that the open reading frame (ORF) predicted from the cDNA sequence analysis is indeed responsible for cell killing, the plasmid pMT-grimORF which directs metal inducible expression of the predicted 138 amino acid protein, SEQ ID NO:2, was tested. As illustrated in Table 4, this construct encodes levels of apoptotic activity that are indistinguishable from the full length cDNA.

This culture system was also used to more directly test the effects of p35 upon grim-induced cell killing. A metal inducible version of p35 called pMT-p35 was used. Consistent with the observed alterations in the developing eye (FIG. 1B), co-expression of p35 completely abrogated grim mediated apoptosis in this context as well (Table 4). This result indicates that the function of grim may reside upstream of one or more ICE-like proteases that are targeted by p35.

Figure 2A:
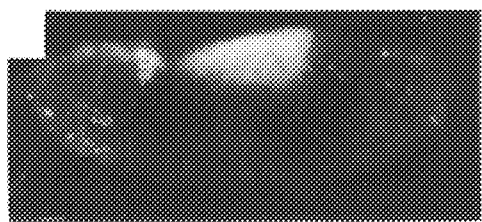
FIG. 2A. Acridine orange staining of wild type stage 13/14 embryos after 30 minute heat treatment.
Figure 2D:
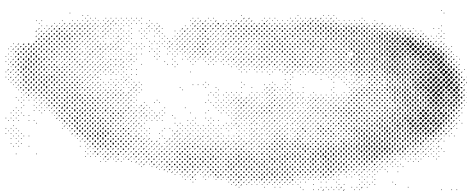
FIG. 2D. Apoptosis one hour after a 30 minute heat treatment in yw, wild-type, stage 9 embryos labeled with TUNEL.
Figure 2B:
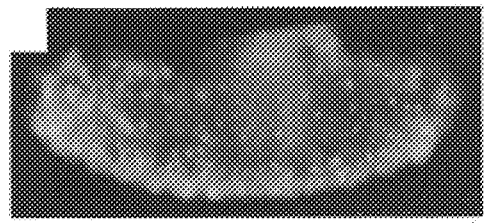
FIG. 2B. Apoptosis induced by rpr one hour after a 30 minute heat treatment in H99 stage 13/14 embryos which contain a heat inducible rpr transgene, hsrpr, and are stained with acridine orange.

Germline transformants also were produced with a heat-inducible transgene, HS-grim and it was found that ectopic expression of grim in this context also caused extensive cell death throughout the embryo (2 independent strains tested). Within 1 hour of heat treatment, excessive apoptosis was scored by acridine orange and TUNEL staining (FIG. 2C and FIG. 2F) in more than 70% of HS-grim embryos whereas no appreciable elevation of apoptosis was observed in control embryos that were heat shocked but lacked the transgene (FIG. 2A and FIG. 2D) [see also White, et al., 1994; Grether, et al., 1995]. Gross morphological abnormalities as a consequence of ectopic cell death and severe organismal lethality were two additional phenotypes associated with heat-induced grim expression. After heat treatment, none of 197 HS-grim embryos tested hatched; whereas more than 85% of 187 control (yw parental strain) embryos exposed in parallel did. Further tests have shown that of approximately 1800 HS-grim embryos receiving heat treatment, none hatched.

Figure 2E:
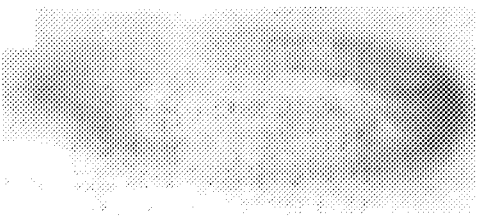
FIG. 2E. Apoptosis induced by rpr one hour after a 30 minute heat treatment in H99 stage 9 embryos bearing a heat inducible rpr transgene, hsrpr and labeled for apoptotic cells by TUNEL.
Figure 2C:
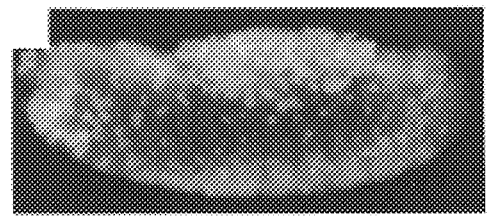
FIG. 2C. Apoptosis induced by grim one hour after a 30 minute heat treatment in stage 13/14 embryos which contain a heat inducible grim transgene, HS-grim and are stained with acridine orange.
Figure 2F:
FIG. 2F. Apoptosis induced by grim one hour after a 30 minute heat treatment in stage 9 embryos bearing heat inducible grim transgene, HS-grim and labeled for apoptotic cells by TUNEL.

The conditional phenotypes associated with HS-grim are similar to those documented for HS-rpr transformants [White, et al., 1996]. Hence a detailed comparison of the apoptotic responses of these strains at various embryonic stages was conducted. Interestingly, it was found that induction of HS-grim could trigger substantial cell deaths during early embryogenesis (FIG. 2F) at a time when HS-rpr failed to provoke any apoptotic response (FIG. 2E). Since these are stages prior to the initiation of programmed cell death in wild type embryonic development [Abrams, et al., 1993] TUNEL was used to score cell death and also confirm the apoptotic character of the embryonic cells. While HS-rpr was unable to induce cell death at stage 9 or earlier, many TUNEL positive cells were frequently observed in HS-grim embryos at this stage (FIG. 2F). These findings were corroborated in two independent HS-rpr strains and two independent HS-grim strains and are therefore not dependent upon insertional site effects. The ability of grim to induce cell death in a developmental context where rpr does not suggests that the activity or regulation of these proteins may be distinct.

EXAMPLE 4

The cell death function of grim is independent of rpr and hid

Figure 2G:
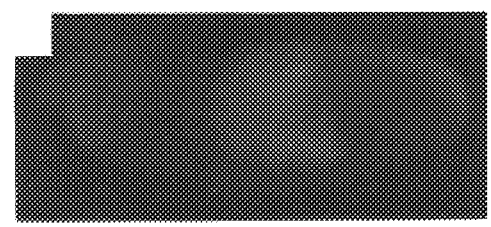
FIG. 2G. Acridine orange staining of heat shocked H99 embryo (H99 region deleted).
Figure 2H:
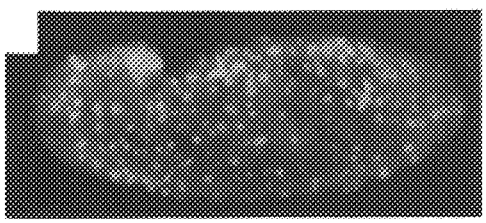
FIG. 2H. Acridine orange staining of grim-induced apoptosis displayed by a heat shocked HS-grim2, H99 embryo (H99 region deleted).

To determine whether grim-induced apoptosis requires other functions in the H99 region, the ability of HS-grim transgenes to trigger cell death in homozygous embryos that are deleted for this interval was determined. In a collection of embryos from parents that are heterozygous for H99 and homozygous for the HS-grim transgene, 25% will be cell death defective and easily scored by an absence of acridine orange staining. After heat treatment, however, prominent acridine orange staining occurred in 100% of embryos from parents of this genotype (as in FIG. 2C) suggesting that grim-induced apoptosis occurred even in embryos homozygous for H99. At later embryonic stages the hid defect could still be distinguished even though cell death was restored to H99 homozygotes. FIG. 2G and FIG. 2H illustrate this observation showing that within one hour after heat treatment, induced grim expression is sufficient to trigger extensive cell death among embryos that bear the characteristic hid phenotype. Appreciable induction of apoptosis does not occur in the absence of heat shock nor does it occur in heat shocked embryos from the parental strains. Moreover, several unrelated control transgenes (including engrailed, hedgehog and disco) also expressed from the hsp70 promoter have been similarly tested and these do not trigger apoptosis in H99 embryos [Grether, et al., 1995]. The data clearly show that grim-induced apoptosis does not require the function of other cell death genes in the H99 interval.

Since expression of rpr RNA anticipates both normal programmed cell death [White, et al., 1994] and ectopically induced apoptosis the possibility that grim-induced cell death might be associated with cross-regulation at the rpr locus was investigated. However, when HS-grim embryos were examined after heat shock by in situ hybridization for altered expression of rpr, no significant effects upon the distribution of rpr RNA were observed. Conversely, it was also possible that the functions of rpr and hid might influence grim expression. grim RNA expression in heat shocked hsrpr embryos [White, et al., 1996] and in embryos homozygous for $hid^{WR+X1}$, a null mutation in hid [Abbot and Lengyel, 1991; Grether, et al., 1995], was examined. Again, no evidence for cross-regulatory interactions was obtained as the distribution of grim RNA in both instances was indistinguishable from wild type. Taken together, these results establish that grim functions independently of rpr or hid as an activator of programmed cell death.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abbot, M. K. and J. A. Lengyel. 1991. Embryonic head involution and rotation of the male terminalia require the Drosophila locus head involution defective. *Genetics* 129: 783–789.

Abrams, J. M., K. White, L. Fessler and H. Steller. 1993. Programmed cell death during Drosophila embryogenesis. *Development* 117: 29–44.

Altschul, S. F., W. Gish, W. Miller, E. W. Myers and D. J. Lipman. 1990. Basic local alignment search tool. *J. Mol. Biol.* 215: 403–410.

Ashburner, M. 1989. Drosophila: A laboratory manual. Cold Spring Harbor Laboratory Press, Cold Spring Harbor, N.Y.

Bump, N. J., M. Hackett, M. Hugunin, S. Seshagiri, K. Brady, P. Chen, C. Ferenz, S. Franklin, T. Ghayur, P. Li, P. Licari, J. Mankovich, L. F. Shi, A. H. Greenberg, L. K.

Miller and W. W. Wong. 1995. Inhibition of ICE family proteases by baculovirus antiapoptotic protein p35. *Science* 269: 1885–1888.

Bunch, T. A., Y. Grinblat and L. S. Goldstein. 1988. Characterization and use of the Drosophila metallothionein promoter in cultured Drosophila melanogaster cells. *Nuc Acids Res* 16: 1043–61.

Campos-Ortega, J. A. and V. Hartenstein. 1985. The embryonic develpment of *Drosophila melanogaster*. Springer-Verlag, Berlin, Germany.

Chirgwin, J. M., A. E. Przybyla, R. J. MacDonald and W. J. Rutter. 1979. Isolation of biologically active ribonucleic acid from sources enriched in ribonuclease. *Biochemistry* 18: 5294–9.

Clem, R. J., M. Fechheimer and L. K. Miller. 1991. Prevention of apoptosis by a baculovirus gene during infection of insect cells. *Science* 254: 1388–1390.

Cleveland, J. L. and J. N. Ihle. 1995. Contenders in FasL/TNF death signaling. *Cell* 81: 479–82.

Ellis, R. E., J. Yuan and H. R. Horvitz. 1991. Mechanisms and functions of cell death. *Annu. Rev. Cell. Biol.* 7: 663–698.

Gavrieli, Y., Y. Sherman and S. A. Ben-Sasson. 1992. Identification of programmed cell death in situ via specific labeling of nuclear DNA fragmentation. *J. Cell. Biol.* 119: 493–501.

Golstein, P., D. Marguet and V. Depraetere. 1995. Fas bridging cell death and cytotoxicity: the reaper connection. *Immunol. Rev.* 146: 45–56.

Golstein, P., D. Marguet and V. Depraetere. 1995. Homology between Reaper and the cell death domains of Fas and TNFR1. *Cell* 81: 185–186.

Gougen, M. and L. Montagnier. 1993. Apoptosis and AIDS. *Science* 260: 1269–1270.

Grether, M. 1994. Molecular genetic analysis of larval visual system development and programmed cell death in Drosophila. Ph.D. Thesis Massachusetts Insitute of Technology.

Grether, M., J. M. Abrams, J. Agapite, K. White and H. Steller. 1995. The head involution defective gene of *Drosophila melanogaster* and its role in programmed cell death. *Genes and Development* 9: 1694–1708.

Hay, B., T. Wolff and G. M. Rubin. 1994. Expression of the baculovirus p35 prevents cell death in *Drosophila*. *Development* 120: 2121–2129.

Hsu, H., J. Xiong and D. V. Goeddel. 1995. The TNF receptor 1-associated protein TRADD signals cell death and NF-kappa B activation. *Cell* 81: 495–504.

Hurle, J. M. 1988. Cell death in developing systems. *Meth. Achiev. exp. Pathol.* 13: 55–86.

Kerr, J. F. R. and B. V. Harmon, 1991, Definition and incidence of apoptosis: an historical perspective, Apoptosis: the molecular basis of cell death, 5–29, Cold Spring Harbor Laboratory Press, New York.

Kerr, J. F. R., A. H. Wyllie and A. R. Currie. 1972. Apoptosis: a basic biological phenomenon with wide ranging implications in tissue kinetics. *Br. J Cancer.* 26: 239–257.

Kramer, H. and M. Phistry. 1996. Mutations in the *Drosophila hook* gene inhibit endocytosis of the boss transmembrane ligand into multivesicular bodies. *J Cell Biol*. in press.

Krumlauf, R. 1994. Hox genes in vertebrate development. *Cell* 78: 191–201.

Lawrence, P. A. 1992. The making of the fly: The genetics of animal design. Blackwell Scientific Publications, London U.K.

Lindsley, D. L. And G. G. Zimm. 1992. The genome of *Drosophila melanogaster*. Acedemic Press, San Diego, Calif.

Liston, P., N. Roy, K. Tamai, C. Lefebvre, S. Baird, G. Chertonhorvat, R. Farahani, M. Mclean, J. E. Ikeda, A. Mackenzie and R. G. Korneluk. 1996. Suppression of apoptosis in mammalian cells by naip and a related family of iap genes. *Nature* 379: 349–353.

Meyaard, L., S. A. Otto, R. R. Jonker, M. J. Mijinster, R. P. M. Keet and F. Miedema. 1992. Programmed cell death of T cells in HIV-1 infection. *Science* 257: 217–219.

Miura, M., H. Zhu, R. Rotello, E. A. Hartwig and J. Yuan. 1993. Induction of apoptosis in fibroblasts by IL-1B-converting enzyme, a mammalian homolog of the C. elegans cell death gene ced-3. *Cell* 75: 653–650.

Oppenheim, R. W. 1991. Cell death during development of the nervous system. *Ann. Rev. Neurosci.* 14: 453–501.

Poole, S. J., L. M. Kauvar, B. Drees and T. Kornberg. 1985. The engrailed locus of Drosophila: structural analysis of an embryonic transcript. *Cell* 40: 37–43.

Pronk, G. J., K. Ramer, P. Amiri and L. T. Williams. 1996. Requirement of an ice-like protease for induction of apoptosis and ceramide generation by reaper. *Science* 271: 808–810.

Rabizadeh, S., D. J. LaCount, P. D. Friesen and D. E. Bredesen. 1993. Expression of the baculovirus p35 gene inhibits mammalian neural cell death. *J Neurochem.* 61: 2318–2321.

Raff, M. C. 1992. Social controls on survival and cell death. *Nature* 356: 397–400.

Rost, B. and C. Sander. 1994. Combining evolutionary information and neural networks to predict protein secondary structure. *Proteins* 19: 55–72.

Roy, N., M. S. Mahedevan, M. McLean, G. Shutler, Z. Yaraghi, R. Farahani, S. Baird, A. Besner-Johnson, C. Lefebvre, K. Xiaolin, M. Salih, H. Aubry, K. Tamai, X. Guan, P. Ioannou, T. O. Crawford, P. Jong, L. Surh, J. Ikeda, R. G. Komeluk and A. Mackenzie. 1995. The gene for neuronal apoptosis inhibitory protein is partially deleted in individuals with spinal muscular atrophy. *Cell* 80: 167–178.

Rubin, G. M. and A. C. Spradling. 1982. Genetic transformation of Drosophila with transposable element vectors. *Science* 218: 348–353.

Sambrook, J., E. F. Fritsch and T. Maniatis. 1989. Molecular cloning: A laboratory manual. Cold Spring Harbor Laboratory Press, Cold Spring Harbor, N.Y.

Saunders, J. W., Jr. and J. F. Fallon, 1967, Cell death in morphogenesis, Major problems in Developmental Biology, M. Locke, 289–314, Academic Press, New York Schneider, I. 1972. Cell lines derived from the late embryonic stages of *Drosophila melanogaster. J. Embryol. Exp. Morphol.* 27: 353–356.

Steller, H. 1995. Mechanisms and Genes of Cellular Suicide. *Science* 267: 1445–1449. Sugimoto, A., P. D. Friesen and J. H. Rothman. 1994. Baculovirus p35 prevents developmentally programmed cell death and rescues a ced-9 mutant in the nematode *Caenorhabditis elegans. EMBO J.* 13: 2023–2028.

Tautz, D. and C. Pfeifle. 1989. A non-radioactive in situ hybridization method for the localization of specific RNAs in Drosophila embryos reveals translational control of the segmentation gene hunchback. *Chromosoma* 98: 81–85.

Tounekti, O., J. Belehradek and L. M. Mir. 1995. Relationships betweeen DNA fragmentation, chromatin condensation and changes in flow cytometry profiles detected during apoptosis. *Experimental cell research* 217: 506–516.

Truman, J. 1984. Cell death in invertebrate nervous systems. *Ann. Rev. Neurosci.* 7: 171–188.

Van der Straten, A., H. Johansen, M. Rosenburg, R. Sweet. 1989. Novel hygromycin B selection system for overexpression of a heterologous gene in *Drosophila melanogaster* cultured cells. *Curr. Meth. Miol. Biol.* 1: 1–8.

Vito, P., E. Lacana and L. Dadamio. 1996. Interfering with apoptosis—ca2+-binding protein alg-2 and alzheimers disease gene alg-3. *Science* 271: 521–525.

White, K., E. Tahaoglu and H. Steller. 1996. Cell killing by the drosophila gene reaper. *Science* 271: 805–807.

Williams, G. T. 1991. Programmed cell death: Apoptosis and oncogenesis. *Cell* 65: 1097–1098.

Wyllie, A. H., J. F. R. Kerr and A. R. Currie. 1980. Cell death: the significance of apoptosis. *Int. Rev. Cytol.* 68: 251–306.

Xue, D. and H. R. Horvitz. 1995. Inhibition of the *Caenorhabditis elegans* cell-death protease CED-3 by a CED-3 cleavage site in baculovirus p35 protein. *Nature* 377: 248–251.

Xue, D. and H. R. Horvitz. 1995. Inhibition of the *Caenorhabditis elegans* cell-death protease CED-3 by a CED-3 cleavage site in baculovirus p35 protein. *Nature* 377: 248–251.

Zhou, L., H. Hashimi, L. M. Schwartz and J. R. Nambu. 1995. Programmed cell death in the Drosophila central nervous system midline. *Current Biology* 5: 784–90.

---

What is claimed is:

1. An isolated nucleic acid segment or its complement, wherein said segment encodes a Drosophila apoptosis inducing polypeptide comprising the amino acid sequence of SEQ ID NO:2, or a conservative substitution variant thereof.

2. An isolated nucleic acid segment according to claim 1, wherein said apoptosis inducing polypeptide has the amino acid sequence of SEQ ID NO:2.

3. An isolated nucleic acid segment according to claim 1, wherein said segment comprises a nucleic acid sequence including the coding region of SEQ ID NO:1 or its complement.

4. An isolated nucleic acid segment according to claim 1, fuirther defined as a nucleic acid having a sequence as set forth in SEQ ID NO:1 or its complement.

5. An isolated nucleic acid segment according to claim 1, wherein said segment is operatively linked to a promoter.

6. An isolated nucleic acid segment according to claim 5, wherein said promoter is a heterologous promoter.

7. An isolated nucleic acid segment according to claim 6, wherein said heterologous promoter is an inducible promoter.

8. An isolated nucleic acid segment according to claim 7, wherein said inducible promoter is a heat shock protein promoter, a radiation inducible promoter or a metal inducible promoter.

9. An isolated nucleic acid segment according to claim 8, wherein said inducible promoter is an hsp70 promoter.

10. An isolated nucleic acid segment according to claim 8, wherein said inducible promoter is a metallothionein promoter.

11. The nucleic acid segment of claim 1 contained in a recombinant vector.

12. The nucleic acid segment of claim 11, wherein said vector is a recombinant expression vector capable of expressing an apoptosis inducing polypeptide on introduction into a host cell.

13. A recombinant host cell comprising the nucleic acid segment of claim 1.

14. A recombinant host cell of claim 13, wherein said nucleic acid segment is introduced into the cell by means of a recombinant vector.

15. The host cell of claim 13, further defined as an insect cell.

16. An isolated nucleic acid, of a size between about 13 and about 100 bases in length, identical in sequence to a portion of a nucleic acid sequence of SEQ ID NO:1 or its complement.

17. An isolated nucleic acid of claim 16, further defined as of a size between about 17 and about 100 bases in length.

18. An isolated nucleic acid, of a size between 16 and about 100 bases in length, that will bind under high stringency conditions to a nucleic acid having a sequence of SEQ ID NO:1 or its complement.

19. A method of making a Drosophila apoptosis inducing polypeptide comprising the steps of:
   a) obtaining an expression vector containing a nucleic acid sequence encoding an apoptosis inducing polypeptide comprising an amino acid sequence of SEQ ID NO:2 or a conservative substitution variant thereof wherein said nucleic acid sequence is operatively linked to a promoter;
   b) transfecting said vector into a host cell; and
   c) culturing said cell under conditions effective to express said apoptosis inducing polypeptide.

20. The method of claim 19, wherein said promoter is an inducible promoter.

21. The method of claim 19, further comprising the step of isolating said apoptosis inducing polypeptide.

22. The method of claim 19, wherein said apoptosis inducing polypeptide has the amino acid sequence of SEQ ID NO:2.

* * * * *

UNITED STATES PATENT AND TRADEMARK OFFICE
CERTIFICATE OF CORRECTION

PATENT NO.   : 5,846,768
DATED        : December 8, 1998
INVENTOR(S)  : Abrams et al.

It is certified that error appears in the above-identified patent and that said Letters Patent is hereby corrected as shown below:

In claim 16, column 44, line 8, delete "13", and insert the following therefor: -- 14 --.

In claim 18, column 44, line 14, delete "16", and insert the following therefor: -- 17 --.

Signed and Sealed this

Sixth Day of April, 1999

Attest:

Q. TODD DICKINSON

*Attesting Officer*          *Acting Commissioner of Patents and Trademarks*